(12) United States Patent
Suslov

(10) Patent No.: US 7,589,473 B2
(45) Date of Patent: Sep. 15, 2009

(54) PULSED PLASMA DEVICE AND METHOD FOR GENERATING PULSED PLASMA

(75) Inventor: Nikolay Suslov, Vastra Frolonda (SE)

(73) Assignee: Plasma Surgical Investments, Ltd., Tortula (VG)

( * ) Notice: Subject to any disclaimer, the term of this patent is extended or adjusted under 35 U.S.C. 154(b) by 221 days.

(21) Appl. No.: 11/890,938

(22) Filed: Aug. 6, 2007

(65) Prior Publication Data
US 2009/0039790 A1    Feb. 12, 2009

(51) Int. Cl.
H05B 31/26    (2006.01)
(52) U.S. Cl. .............. 315/111.21; 315/111.01; 315/111.11
(58) Field of Classification Search ............ 315/111.01, 315/111.11, 111.21, 111.81, 111.91, 500, 315/507, 84.51, 84.61
See application file for complete search history.

(56) References Cited

U.S. PATENT DOCUMENTS

| | | | |
|---|---|---|---|
| 3,082,314 | A | 3/1963 | Yoshiaki et al. |
| 3,145,287 | A | 8/1964 | Seibein et al. |
| 3,360,988 | A | 1/1968 | Stein et al. |
| 3,413,509 | A | 11/1968 | Cann et al. |
| 3,433,991 | A | 3/1969 | Whyman |
| 3,434,476 | A | 3/1969 | Shaw et al. |
| 3,676,638 | A | 7/1972 | Stand |
| 3,803,380 | A | 4/1974 | Ragaller |
| 3,838,242 | A | 9/1974 | Goucher |
| 3,851,140 | A | 11/1974 | Coucher |
| 3,903,891 | A | 9/1975 | Brayshaw |
| 3,914,573 | A | 10/1975 | Muehlberger |

(Continued)

FOREIGN PATENT DOCUMENTS

CA    1 144 104    4/1983

(Continued)

OTHER PUBLICATIONS

Asawanonda et al., 2000, "308-nm excimer laser for the treatment of psoriasis: a dose-response study." Arach. Dermatol. 136:619-24.

(Continued)

Primary Examiner—Douglas W Owens
Assistant Examiner—Jianzi Chen
(74) Attorney, Agent, or Firm—Jones Day

(57) ABSTRACT

A device and a method for generating a truly pulsed plasma flow are disclosed. The device includes a cathode assembly comprising a cathode and a cathode holder, an anode, and two or more intermediate electrodes, the anode and the intermediate electrodes forming a plasma channel expanding toward the anode. The intermediate electrode closest to the cathode may form a plasma chamber around the cathode tip. An extension nozzle forming an extension channel having a tubular insulator along at least a portion of its interior surface is affixed to the anode end of the device.

During operation, a voltage is applied between the cathode and the anode and a current is passed through the cathode, the plasma, and the anode. The voltage and current profiles are selected to cause the rapid development of a plasma flow with required characteristics. A substantially uniform temperature and power density distribution of the plasma pulse is achieved in the extension nozzle. Additionally, ozone may be generated in the extension nozzle during the generation of the plasma pulse.

21 Claims, 17 Drawing Sheets

U.S. PATENT DOCUMENTS

| | | |
|---|---|---|
| 3,938,525 A | 2/1976 | Coucher |
| 3,991,764 A | 11/1976 | Incropera et al. |
| 4,035,684 A | 7/1977 | Svoboda et al. |
| 4,256,779 A | 3/1981 | Sokol et al. |
| 4,317,984 A | 3/1982 | Fridlyand |
| 4,445,021 A | 4/1984 | Irons et al. |
| 4,661,682 A | 4/1987 | Gruner et al. |
| 4,672,163 A | 6/1987 | Matsui et al. |
| 4,674,683 A | 6/1987 | Fabel |
| 4,696,855 A | 9/1987 | Pettit, Jr et al. |
| 4,711,627 A | 12/1987 | Oeschsle et al. |
| 4,743,734 A | 5/1988 | Garlanov et al. |
| 4,764,656 A | 8/1988 | Browning |
| 4,780,591 A | 10/1988 | Bernecki et al. |
| 4,781,175 A | 11/1988 | McGreevy et al. |
| 4,784,321 A | 11/1988 | Delaplace |
| 4,785,220 A | 11/1988 | Brown et al. |
| 4,839,492 A | 6/1989 | Bouchier et al. |
| 4,841,114 A | 6/1989 | Browning |
| 4,853,515 A | 8/1989 | Willen et al. |
| 4,855,563 A | 8/1989 | Beresnev et al. |
| 4,866,240 A | 9/1989 | Webber |
| 4,869,936 A | 9/1989 | Moskowitz et al. |
| 4,874,988 A | 10/1989 | English |
| 4,877,937 A | 10/1989 | Muller |
| 4,916,273 A | 4/1990 | Browning |
| 4,924,059 A | 5/1990 | Rotolico et al. |
| 5,008,511 A | 4/1991 | Ross |
| 5,013,883 A | 5/1991 | Fuimefreddo et al. |
| 5,144,110 A | 9/1992 | Marantz et al. |
| 5,225,652 A | 7/1993 | Landes |
| 5,227,603 A | 7/1993 | Doolette et al. |
| 5,285,967 A | 2/1994 | Weidman |
| 5,332,885 A | 7/1994 | Landes |
| 5,396,882 A | 3/1995 | Zapol |
| 5,406,046 A | 4/1995 | Landes |
| 5,408,066 A | 4/1995 | Trapani et al. |
| 5,412,173 A | 5/1995 | Muehlberger |
| 5,452,854 A | 9/1995 | Keller |
| 5,485,721 A | 1/1996 | Steenborg |
| 5,514,848 A | 5/1996 | Ross et al. |
| 5,519,183 A | 5/1996 | Mueller |
| 5,573,682 A | 11/1996 | Beason, Jr. |
| 5,620,616 A | 4/1997 | Anderson et al. |
| 5,629,585 A | 5/1997 | Altmann et al. |
| 5,637,242 A | 6/1997 | Muehlberger |
| 5,640,843 A | 6/1997 | Aston |
| 5,679,167 A | 10/1997 | Muehlberger |
| 5,680,014 A | 10/1997 | Miyamoto et al. |
| 5,720,745 A | 2/1998 | Farin et al. |
| 5,837,959 A | 11/1998 | Muehlberger et al. |
| 5,843,079 A | 12/1998 | Suslov |
| 5,858,469 A | 1/1999 | Sahoo et al. |
| 5,858,470 A | 1/1999 | Bernecki et al. |
| 5,897,059 A | 4/1999 | Muller |
| 5,932,293 A | 8/1999 | Belashchenko et al. |
| 6,003,788 A | 12/1999 | Sedov |
| 6,042,019 A | 3/2000 | Rusch |
| 6,114,649 A | 9/2000 | Delcea |
| 6,137,078 A | 10/2000 | Keller |
| 6,181,053 B1 | 1/2001 | Roberts |
| 6,202,939 B1 | 3/2001 | Delcea |
| 6,273,789 B1 | 8/2001 | LaSalle et al. |
| 6,283,386 B1 | 9/2001 | Van Steenkiste et al. |
| 6,386,140 B1 | 5/2002 | Muller et al. |
| 6,392,189 B1 | 5/2002 | Delcea |
| 6,443,948 B1 | 9/2002 | Suslov |
| 6,475,215 B1 | 11/2002 | Tanrisever |
| 6,515,252 B1 | 2/2003 | Girold |
| 6,528,947 B1 | 3/2003 | Chen et al. |
| 6,548,817 B1 | 4/2003 | Anders |
| 6,657,152 B2 | 12/2003 | Shimazu |
| 6,669,106 B2 | 12/2003 | Delcea |
| 6,676,655 B2 | 1/2004 | McDaniel |
| 6,845,929 B2 | 1/2005 | Dolatabadi et al. |
| 6,886,757 B2 | 5/2005 | Byrnes et al. |
| 6,958,063 B1 | 10/2005 | Soll et al. |
| 6,972,138 B2 | 12/2005 | Heinrich et al. |
| 6,986,471 B1 | 1/2006 | Kowalsky et al. |
| 7,030,336 B1 | 4/2006 | Hawley |
| 7,491,907 B2 * | 2/2009 | Kowalsky et al. ......... 219/76.16 |
| 2001/0041227 A1 | 11/2001 | Hislop |
| 2002/0071906 A1 | 6/2002 | Rusch |
| 2002/0097767 A1 | 7/2002 | Krasnov |
| 2003/0030014 A1 | 2/2003 | Wieland et al. |
| 2003/0075618 A1 | 4/2003 | Shimazu |
| 2003/0178511 A1 | 9/2003 | Dolatabadi et al. |
| 2003/0190414 A1 | 10/2003 | Van Steenkiste |
| 2004/0018317 A1 | 1/2004 | Heinrich et al. |
| 2004/0116918 A1 | 6/2004 | Konesky |
| 2004/0124256 A1 | 7/2004 | Itsukaichi et al. |
| 2004/0129222 A1 | 7/2004 | Nylen et al. |
| 2004/0195219 A1 | 10/2004 | Conway |
| 2005/0082395 A1 | 4/2005 | Gardega |
| 2005/0120957 A1 | 6/2005 | Kowalsky et al. |
| 2005/0255419 A1 | 11/2005 | Belashchenko et al. |
| 2006/0004354 A1 | 1/2006 | Suslov |
| 2006/0037533 A1 | 2/2006 | Belashchenko et al. |
| 2006/0049149 A1 | 3/2006 | Shimazu |
| 2006/0090699 A1 | 5/2006 | Muller |
| 2006/0091116 A1 | 5/2006 | Suslov |
| 2006/0091117 A1 | 5/2006 | Blankenship et al. |
| 2006/0091119 A1 | 5/2006 | Zajchowski et al. |
| 2006/0108332 A1 | 5/2006 | Belashchenko |
| 2007/0021748 A1 | 1/2007 | Suslov |
| 2007/0138147 A1 | 6/2007 | Molz et al. |

FOREIGN PATENT DOCUMENTS

| | | |
|---|---|---|
| CA | 1 308722 | 10/1992 |
| CN | 1557731 | 12/2004 |
| DE | 10127261 | 9/1993 |
| DE | 4209005 | 12/2002 |
| EP | 0 282 677 | 9/1988 |
| EP | 0 411 170 | 2/1991 |
| EP | 0 748 149 | 12/1996 |
| EP | 0851040 | 7/1998 |
| FR | 2 193 299 | 2/1974 |
| FR | 2 567 747 | 1/1986 |
| GB | 751735 | 7/1956 |
| GB | 921016 | 3/1963 |
| GB | 1 125 806 | 9/1968 |
| GB | 1 176 333 | 1/1970 |
| GB | 1 268 843 | 3/1972 |
| GB | 2407050 | 4/2005 |
| JP | 62123004 | 6/1987 |
| JP | 1198539 | 8/1989 |
| JP | 3 043 678 | 2/1991 |
| JP | 9299380 | 11/1997 |
| JP | 10024050 | 1/1998 |
| JP | 10234744 | 9/1998 |
| MX | PA04010281 | 6/2005 |
| RU | 2178684 | 1/2002 |
| RU | 2183480 | 6/2002 |
| RU | 2183946 | 6/2002 |
| WO | WO 92/19166 | 11/1992 |
| WO | WO 96/06572 | 3/1996 |
| WO | WO 97/11647 | 4/1997 |
| WO | WO 01/62169 | 8/2001 |
| WO | WO 02/30308 | 4/2002 |
| WO | WO 2004/030551 | 4/2004 |
| WO | WO 2004/105450 | 12/2004 |
| WO | WO 2005/099595 | 10/2005 |
| WO | WO 2006/012165 | 2/2006 |

| WO | WO 2007/006516 | 1/2007 |
| WO | WO 2007/006517 | 1/2007 |
| WO | WO 2007/040702 | 4/2007 |

OTHER PUBLICATIONS

Coven et al., 1999, "PUVA-induced lymphocyte apoptosis: mechanism of action in psoriasis." Photodermatol. Photoimmunol. Photomed. 15:22-7.

Dabringhausen et al., 2002, "Determination of HID electrode falls in a model lamp I: Pyrometric measurements." J. Phys. D. Appl. Phys. 35:1621-1630.

Davis J.R. (ed) ASM Thermal Spray Society, Handbook of Thermal Spray Technology, 2004, U.S. 42-168.

Feldman et al., 2002, "Efficacy of the 308-nm excimer laser for treatment of psoriasis: results of a multicenter study." J. Am Acad. Dermatol. 46:900-6.

Gerber et al., 2003, "Ultraviolet B 308-nm excimer laser treatment of psoriasis: a new phototherapeutic approach." Br. J. Dermatol. 149:1250-8.

Honigsmann, 2001, "Phototherapy for psoriasis." Clin. Exp. Dermatol. 26:343-50.

International-type Search report dated Jan. 18, 2006, Swedish App. No. 0501603-5.

International-type Search report dated Jan. 18, 2006, Swedish App. No. 0501602-7.

International-type Search Report, dated Jan. 18, 2006, Swedish App. No. 0501604-3.

Lichtenberg et al., 2002, "Observation of different modes of cathodic arc attachment to HID electrodes in a model lamp." J. Phys. D. Appl. Phys. 35:1648-1656.

PCT International Search Report dated Feb. 14, 2007, International App. No. PCT/EP2006/006688.

PCT International Search Report dated Feb. 22, 2007, International App. No. PCT/EP2006/006689.

PCT International Search Report, dated Feb. 22, 2007, International App. No. PCT/EP2006/006690.

PCT International Search Report, dated Oct. 23, 2007, International App. No. PCT/EP2007/000919.

PCT Written Opinion of the International Searching Authority dated Feb. 14, 2007, International App. No. PCT/EP2006/006688.

PCT Written Opinion of the International Searching Authority dated Feb. 22, 2007, International App. No. PCT/EP2006/006689.

PCT Written Opinion of the International Searching Authority dated Feb. 22, 2007, International App. No. PCT/EP2006/006690.

PCT Written Opinion of the International Searching Authority dated Oct. 23, 2007, International App. No. PCT/EP2007/000919.

Schmitz & Riemann, 2002, "Analysis of the cathode region of atmospheric pressure discharges." J. Phys. D. Appl. Phys. 35:1727-1735.

Trehan & Taylor, 2002, "Medium-dose 308-nm excimer laser for the treatment of psoriasis." J. Am. Acad. Dermatol. 47:701-8.

Office Action dated Oct. 18, 2007 of U.S. Appl. No. 11/701,911.

Office Action dated Feb. 1, 2008 of U.S. Appl. No. 11/482,580.

Office Action dated Apr. 17, 2008 of U.S. Appl. No. 11/701,911.

PCT International Search Report PCT/EP2007/006939, dated May 26, 2008.

PCT Invitation to Pay Additional Fees PCT/EP2007/006940, dated May 20, 2008.

PCT Written Opinion of the International Searching Authority PCT/EP2007/006939, dated May 26, 2008.

PCT Written Opinion of the International Searching Authority PCT/EP2007/006940.

PCT International Search Report PCT/EP2007/006940.

\* cited by examiner

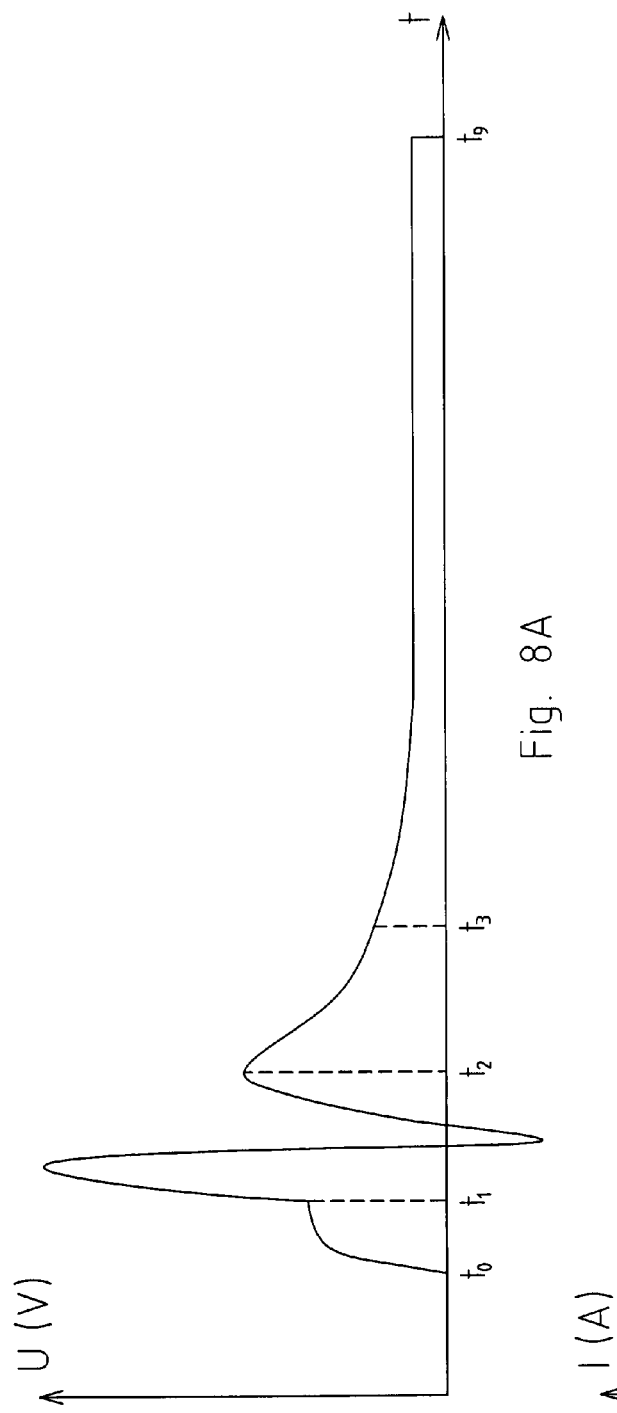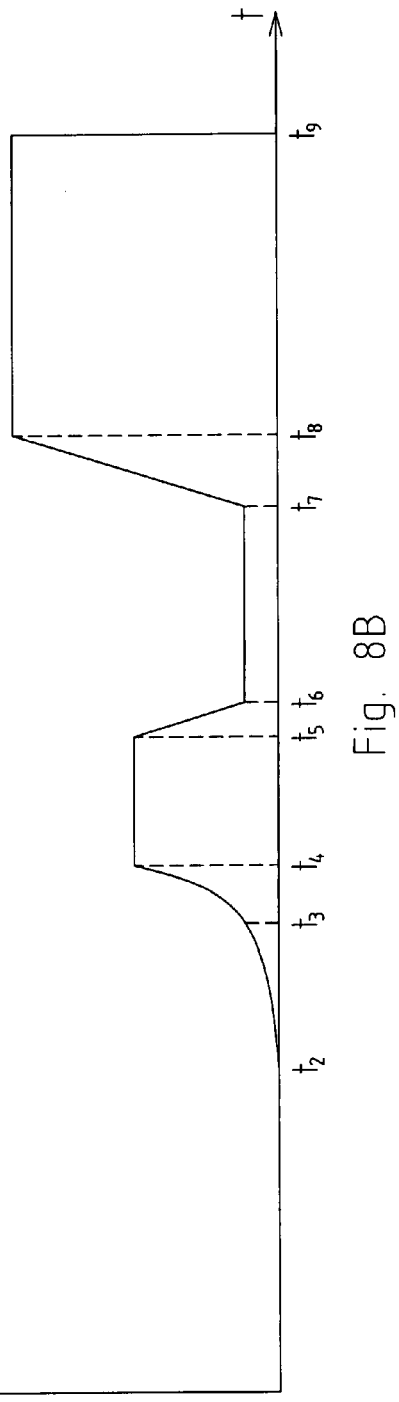

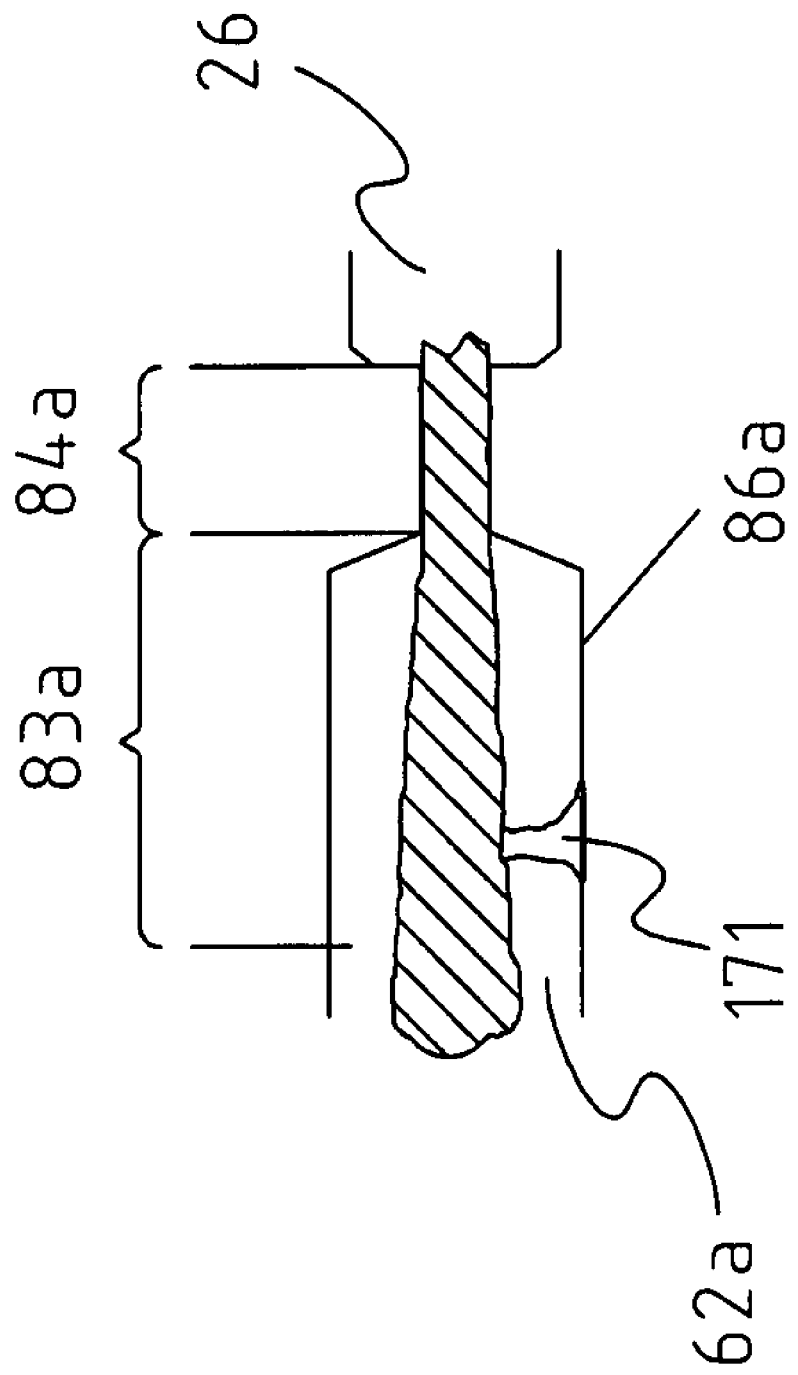

190

PULSED PLASMA DEVICE AND METHOD FOR GENERATING PULSED PLASMA

FIELD OF INVENTION

The present invention relates to plasma generating devices, and more particularly to plasma generating devices and methods for producing pulsed plasma for applications requiring pure plasma.

BACKGROUND

Plasma generating devices play an important role in many areas. For example, plasma is used in displays, such as television sets and computer monitors, spectrography, in spraying applications such as coating, and in medicine.

It is well known in the art that plasma can be effectively used in the medical field for cutting, coagulation, and vaporization of tissues. For best results, the generated plasma has to have precise characteristics, such as velocity, temperature, energy density, etc. Preferably, plasma used for medical applications has to be pure. In other words, it should contain only particles of the ionized plasma generating gas and no other particles, such as materials separated from various parts of the plasma-generating device during operation.

Recently, attempts have been made to use plasma for tissue treatment and particularly skin treatment. Plasma may have different effects when it comes in contact with a skin surface depending on, among others, the temperature increase that it produces on the surface of the skin. For example, increasing the temperature by approximately 35°-38° C. has a wrinkle reducing effect. Increasing the temperature by approximately 70° C. removes the epidermis layer, which may be useful in plastic surgery. It has been recognized that a continuous plasma flow, suitable for cutting, coagulating, and evaporation of tissues, is not suitable for other types of tissue treatment in general, and for skin treatment in particular. Instead, to avoid undesired skin damage that would result from using continuous plasma flow, pulsed plasma is used. Two types of device that may be used for this purpose are presently known in the art.

The device disclosed in U.S. Pat. No. 6,629,974 is an example of the first type. In devices of this type, plasma is generated by passing plasma generating gas, such as nitrogen, through an alternating electric field. The alternating electric field creates a rapid motion of the free electrons in the gas. The rapidly moving electrons strike out other electrons from the gas atoms, forming what is known as an electron avalanche, which in turn creates a corona discharge. By applying the electric field in pulses, pulsed corona discharge is generated. Among the advantages of this method for generating pulsed corona discharge is (1) the absence of impurities in the flow and (2) short start times that enable generation of a truly pulsed flow. For the purposes of this disclosure, a truly pulsed flow refers to a flow that completely ceases during the off period of the pulse.

A drawback of devices and methods of the first type is that the generated corona discharge has a fixed maximum temperature of approximately 2000° C. The corona discharge formed in the device never becomes a high temperature plasma. To achieve the energy of 1-4 Joules required for modifying collagen during skin treatment by a device of this type, the rate of plasma generating gas flow has to be relatively high. For example, using argon in such a device requires a flow of approximately 20 liters/min to achieve the required energy. That flow rate is impracticable for skin treatment. When nitrogen is used for generating plasma, the required energy can be achieved with a flow rate of only about 5 liters/min, but even this rate will create discomfort for a patient. Accordingly, the applications of devices of the first type are limited by the nature of the electrical discharge process that is capable of producing a corona discharge.

Devices of the second type generate plasma by heating the flow of plasma generating gas passing through a plasma channel by an electric arc that is established between a cathode and an anode that forms the plasma channel. An example of a device of the second type is disclosed in U.S. Pat. No. 6,475,215. According to the disclosure of U.S. Pat. No. 6,475,215, as the plasma generating gas, preferably argon, traverses the plasma channel, a pulsed DC voltage is applied between the anode and the cathode. A predetermined constant bias voltage may or may not be added to the pulsed DC voltage. During a voltage pulse, the number of free electrons in the plasma generating gas increases, resulting in a decrease in the resistance of the plasma and an exponential increase of the electric current flowing through the plasma. During the off period, the number of free electrons in the plasma generating gas decreases, resulting in an increase in resistance of the plasma and an exponential decrease in the current flowing through the plasma. Although the current is relatively low during the off period, it never completely ceases. This low current, referred to as the standby current, is undesirable because a truly pulsed plasma flow is not generated. During the off period a continuous low-power plasma flow is maintained. In essence, the device does not generate pulsed plasma, but rather a continuous plasma flow with power spikes, called pulses, thus simulating pulsed plasma. Because the off-period is substantially longer than a pulse, the device outputs a significant amount of energy during the off period and, therefore, it cannot be utilized effectively for applications that require a truly pulsed plasma flow. For example, if the device is used for skin treatment, it may have to be removed from the skin surface after each pulse, so that the skin is not exposed to the low power plasma during the off period. This impairs the usability of the device.

Dropping the current flow through the plasma to zero between pulses and restarting the device for each pulse of plasma is not practicable when using the device disclosed in U.S. Pat. No. 6,475,215. Restarting the device for each pulse would result in the rapid destruction of the cathode, as a result of passing a high current through the cathode without ensuring that cathode arc attachment is well controlled.

The inability of the device disclosed in U.S. Pat. No. 6,475,215, and other devices of this type presently known in the art, to generate a truly pulsed plasma flow that can be safely used on a patient is due to the structure of the device. It takes a few milliseconds to reach a plasma flow phase after the off period. During these few milliseconds the plasma properties are not easily controlled, and therefore it cannot be used on a patient. Additionally, when devices of this type startup there is some erosion of electrodes due to sputtering. This erosion results in separated electrode materials flowing in the plasma. When a continuous plasma flow is used, the startup impurities are a relatively minor drawback, because the startup, and the impurities associated with it, occur only once per treatment. It is therefore possible to wait a few seconds after the startup for the electrode materials to exit the device before beginning actual treatment. However, waiting for impurities to exit the device when using a pulsed plasma flow is impractical, because the next pulse of plasma would have to be generated before the waiting period is over.

When the plasma flow has been previously created it takes just a few microseconds to increase or decrease the current in the plasma flow. Additionally, because there is no startup, impurities do not enter the plasma flow, and there is no stress on the cathode. However, sustaining even a low electrical current through the plasma continuously renders the device suboptimal for some applications that require a truly pulsed plasma flow, as discussed above.

Difficulties in generating a truly pulsed plasma flow by the means of heating the plasma generating gas with an electric arc are primarily due to the nature of processes occurring on the electrodes. In general, and for medical applications especially, it is critical to ensure operation free from the erosion of the anode and the cathode when the current rapidly increases. During the rapid current increase the temperature of the cathode may be low and not easily controlled during subsequent repetitions of the pulse. When generating an electric arc between the cathode and the anode, the area of attachment of the arc to the cathode strongly depends on the initial temperature of the cathode. When the cathode is cold, then the area of attachment is relatively small. After several pulses the temperature of the cathode increases, so that during the period of a rapid current increase the area of attachment expands over the entire surface area of the cathode and even the cathode holder. Under these circumstances the electric potential of the cathode begins to fluctuate and the cathode erosion begins. Furthermore, if the area of attachment of the electric arc reaches the cathode holder it begins to melt thus introducing undesirable impurities into the plasma flow.

A similar situation occurs on the surface of the anode. When the current in the arc increases rapidly, the plasma flow does not have sufficient time to reach a high temperature. As a result, the concentration of plasma close to the anode surface is low. This leads to a drop in the electric potential of the anode and its fluctuation which causes intensive erosion of the cathode. Fluctuations in the electric potentials of the cathode and anode lead to an unstable and not easily controlled energy of the pulsed plasma flow.

For the cathode to function properly it is necessary to control the exact location and the size of the area of attachment of the electric arc to the cathode surface during the periods of rapid current increase in each pulse of plasma. For the proper function of the anode it is necessary to establish the flow of the heated plasma at the surface of the anode during the rapid current increase as well as during the operational period of the pulse.

Generating truly pulsed plasma, especially for medical applications, poses several additional problems. First, as mentioned above, plasma has to be pure, free from any electrode materials or other impurities. Second, properties of the generated pulse of plasma have to be controlled. Initially, by controlling the duration, voltage and current of the pulse the energy transferred by the pulse can be controlled. For some applications, such as skin treatment, merely controlling the energy transferred in the pulse is not enough; the energy and temperature have to be distributed substantially uniformly over the treated area.

Accordingly, presently there is a need for a device that overcomes the limitations of the currently known devices by generating truly pulsed plasma with minimal amounts of impurities, and by substantially uniformly distributing energy transferred in each pulse over the treated area. Additionally, there may be applications where the device optionally needs to be capable of supplying ozone to the treated surface and removing fluids and other extraneous matters from the treated surface.

SUMMARY

The pulsed plasma device of the invention as shown in the drawings comprises a cathode assembly which includes one or more cathodes affixed in a cathode holder, an anode, and two or more intermediate electrodes. The anode and the intermediate electrodes form a plasma channel. The intermediate electrode closest to the cathodes also forms a plasma chamber around the cathode ends closest to the anode. The plasma channel comprises three portions: a heating portion, an expansion portion, and an anode portion. The expansion portion has two or more expansion sections. The diameter of each successive section of the expansion portion increases toward the anode. The anode portion has a diameter that is greater than the diameter of the expansion portion closest to the anode. The cathode holder prevents displacement of the cathodes, preferably keeping them parallel to the axis of the device thus preventing their angular displacement.

An extension nozzle is affixed at the anode end of the device. The extension nozzle forms an extension channel connected to the plasma channel. A tubular insulator element covers a longitudinal portion of the inside surface of the extension channel. Additionally, in some embodiments, the extension nozzle has one or more oxygen carrying gas inlets.

During operation truly pulsed plasma is generated by the device. For each pulse, the plasma passes through three stages: a spark discharge, a glow discharge, and an arc discharge. In an exemplary embodiment, the spark discharge is created by applying a high frequency, high amplitude voltage wave between the cathodes and the anode. After the spark discharge is created between the cathodes and the anode, a preferably transient voltage is applied between the cathodes and the anode and a current is passed through the cathodes, the plasma generating gas, and the anode, which results in generation of the glow discharge. At the end of the glow discharge, when the cathode ends become sufficiently heated, the voltage between the cathodes and the anode drops down marking the beginning of the cathode thermionic electron emission and the beginning of the arc discharge phase. Once the arc discharge phase begins the plasma is attached to all cathodes in the assembly. The current is lowered to decrease the area of plasma attachment to a single cathode. Then after the lowered current is maintained for a period of time, the current is increased to the operational level. After the predetermined duration of the pulse, both the voltage and the current are set to zero for the duration off period. This process is repeated for every pulse.

For medical applications, it is critical that there be no impurities in the plasma. Sputtering from the surface of the cathode holder is eliminated by utilizing a cathode assembly with multiple cathodes and generating pulsed plasma having a controlled area of plasma attachment.

During operation, the plasma flow exiting the anode has an essentially parabolic temperature and energy density distribution. The extension nozzle transforms the temperature and energy distribution to a more uniform distribution that is more suitable for contact with a patient. The thermal insulator located in the extension channel is made of a non-metal material with a low thermal conductivity. When the plasma flows through this thermal insulator, the colder layers of plasma are heated without transferring heat to the elements forming the channel.

Additionally, in embodiments having inlet passages to the nozzle, while the plasma flow traverses the extension channel, it sucks oxygen carrying gas, such as air, into the flow. Under the influence of the high temperature of plasma in the extension channel and the radiation emanating from the plasma channel, ozone is formed in the extension channel. Molecules of ozone, which may have beneficial effects, exit the device together with the plasma and come in contact with the treated skin.

In one embodiment, a device for generating pulses of plasma comprising: an anode; a cathode assembly comprising (i) one or more cathodes, and (ii) a cathode holder; a plasma channel, extending longitudinally between said cathode and through said anode, and having an outlet opening at the anode end, a part of said plasma channel being formed by two or more intermediate electrodes electrically insulated from each other and the anode, the plasma channel comprising a heating portion closest to the cathode, an anode portion, and an expansion portion between the heating portion and the anode portion, the expansion portion having two or more sections with diameters of the sections increasing toward the anode, wherein the minimum number of sections of the heating portion depends on the ratio of the diameter of the plasma channel in the anode portion and the diameter of the plasma channel in the heating portion; a plasma chamber formed by one of the intermediate electrodes, the plasma chamber connected to the cathode end of the plasma channel; and an extension nozzle forming an extension channel connected to the anode end of the plasma channel is disclosed.

Also, a method of treating tissue with pulses of plasma comprising: for each pulse, generating a plasma flow; expanding the plasma flow to a predetermined cross-section; modifying the distribution of thermal energy of the expanded plasma flow so the distribution is substantially uniform in the cross-section; applying the plasma flow to the treated skin; and ceasing the plasma flow is disclosed.

BRIEF DESCRIPTION OF THE DRAWINGS

FIG. 8A illustrates the voltage applied between the cathode and the anode during generation of a plasma pulse;

FIG. 8B illustrates the current passed through the cathode, the plasma, and the anode during generation of the plasma pulse;

FIG. 9 illustrates (1) the widening of the plasma channel that does not result in the full expansion of plasma during the pulse and (2) an electric arc established between the plasma and an intermediate electrode;

DESCRIPTION OF EMBODIMENTS

Figure 1:
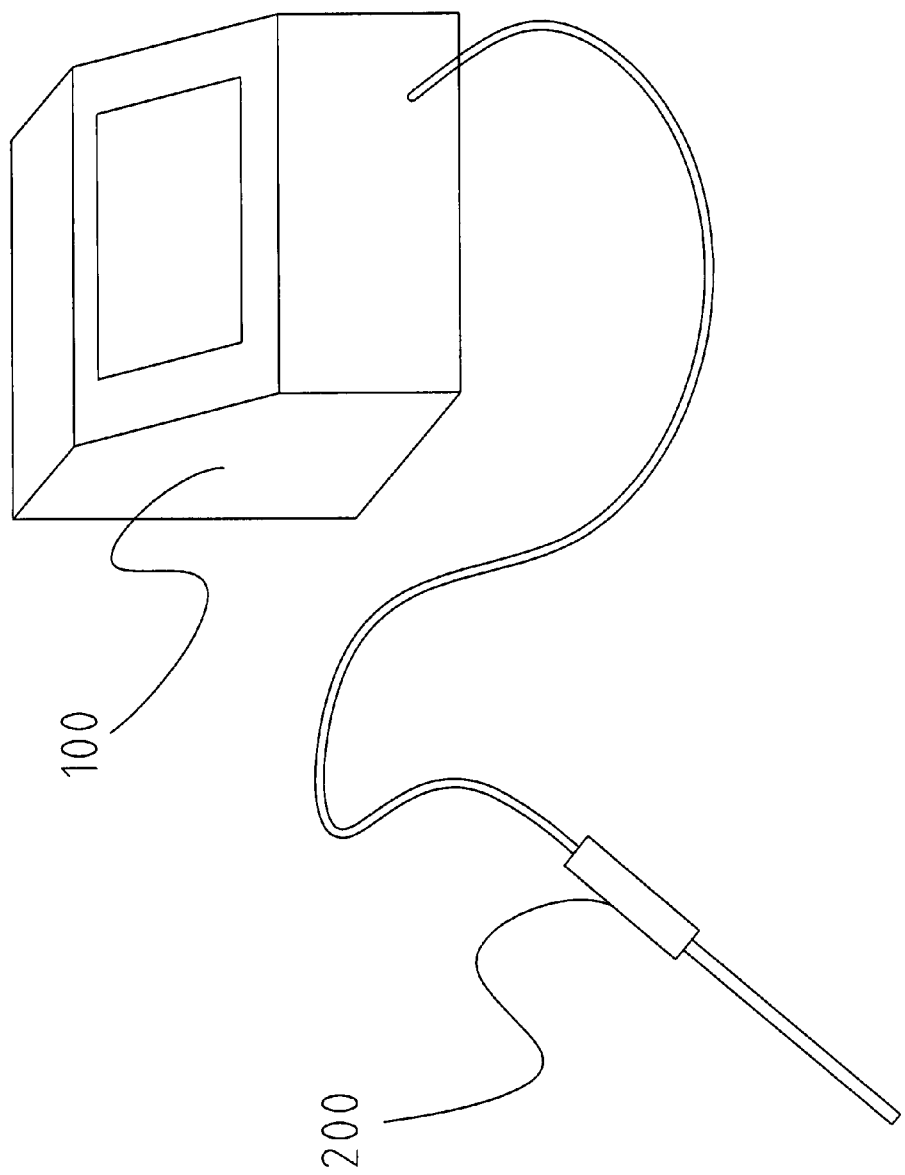
FIG. 1 illustrates a system for generating of pulsed plasma comprising a console and a hand piece.

Referring to FIG. 1, a system for generating pulsed plasma generally comprises a console 100 and a hand piece 200. Hand piece 200 is sometimes referred to herein as the device. Console 100 supplies electricity, plasma generating gas, preferably argon, cooling agents, such as water, and/or oxygen carrying gas, such as air, etc. to hand piece 200. Additionally, console 100 may contain one or more pumps that may be used to remove extraneous matter from the treated surface with the device 200 via one or more suction channels. Console 100 has control circuitry for operating hand piece 200 and a user interface comprised of a display and controls, which are generally known in the art. An operator, such as a trained medical professional, programs the mode of operation of the device with the controls of console 100 in accordance with parameters for a given medical procedure, and then uses hand piece 200 to perform the given procedure. Although the description of embodiments of the present disclosure relates to the medical field, it is understood that other embodiments of the device may be used for other applications unrelated to medicine.

Figure 2A:
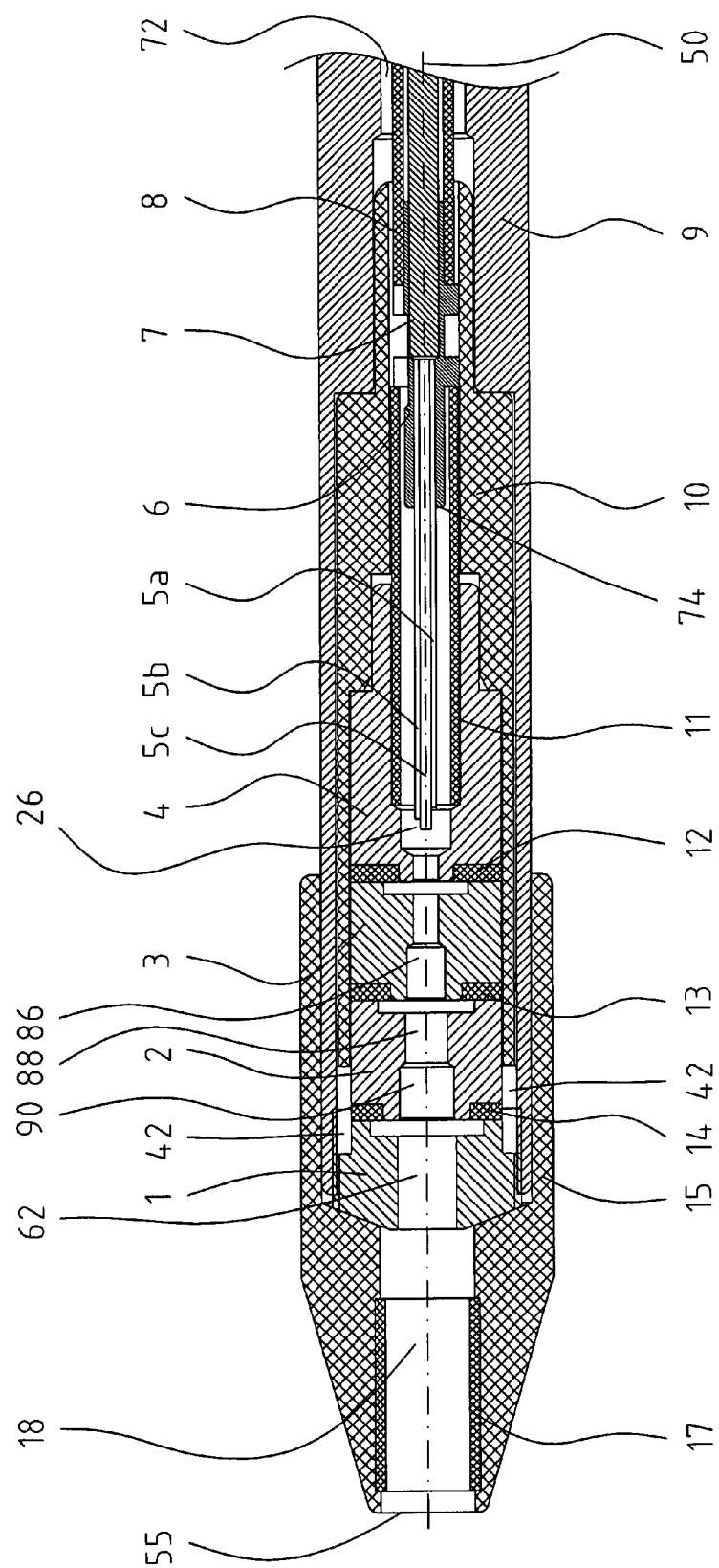
FIG. 2A illustrates a cross sectional longitudinal view of an embodiment of the device.

FIG. 2A shows a longitudinal cross section of one embodiment of the device. In this embodiment, casing 9 forms the outside of the device. Preferably, device 200 is cylindrical and all elements are annular and are arranged coaxially with respect to the axis of the device 50. In some embodiments, however, the device may not be cylindrical and a different internal or external geometry may be used. The embodiment of the device shown in FIG. 2A comprises anode 1 and one or more cathodes 5a, 5b, 5c, preferably made of tungsten containing lanthanum, arranged in a cathode holder 6. The cathode holder 6 prevents undesired angular displacement of the cathode from the axis of the device 50. Cathode holder 6 also holds a portion of conductor 7, which is preferably a rod made of metal with high electric conductivity. Crimping of the components of the cathode assembly together during manufacture is one means for preventing displacement of the cathode along the axis 50. In the preferred embodiment, the entire cathode assembly, comprised of cathodes 5a, 5b, 5c, cathode holder 6, and electric conductor 7, is tightly fitted inside device 200 to prevent any movement of cathodes 5a, 5b, 5c.

Cathode insulator 11 surrounds longitudinal portions of cathode 5a, 5b, 5c. Cathode insulator 11 extends from the surface of the cathode holder 74 closest to the anode on one end to a point part way along the cathodes. Cathode insulator 11 is made of a material that provides both thermal and electrical insulation of cathode 5a, 5b, 5c. Electrical conductor 7 is used to supply electric potential to cathodes 5a, 5b, 5c. Cathodes 5a, 5b, 5c are electrically connected and always have the same electric potential. Insulator element 8 surrounds conductor 7 and a portion of cathode holder 6 as shown in FIG. 2A. Insulator element 8 provides electrical insulation of conductor 7, and is preferably made of vinyl. In operation, a passage 72 enables the flow of the plasma generating gas from console 100 along insulator 8. The gas then flows along space 54 between insulator 8 and water divider 10. Then, the gas flows through groove 56 in cathode holder 6, and then along cathodes 5a, 5b, 5c, inside the cathode insulator 11.

Figure 4:
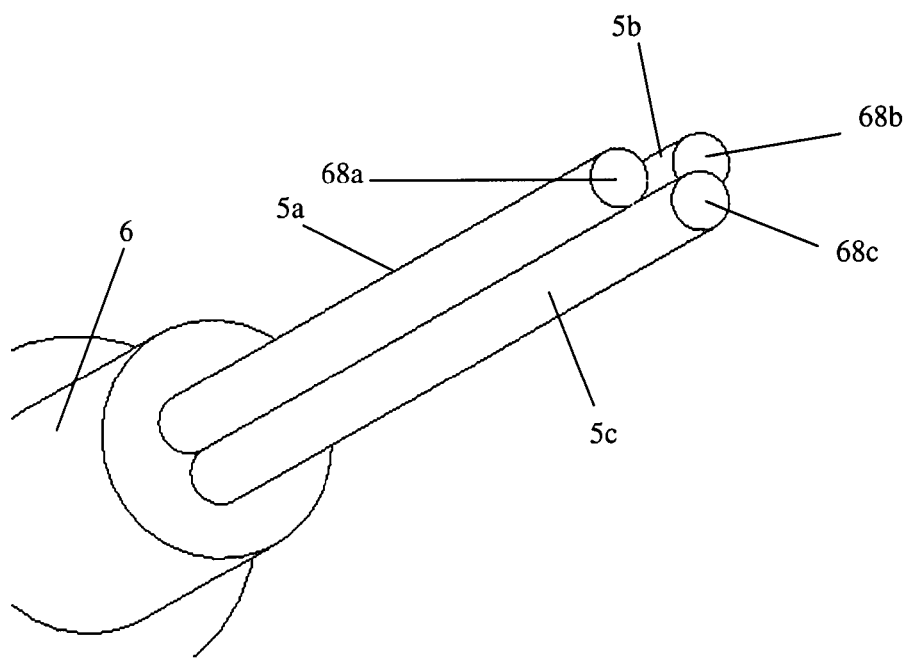
FIG. 4 illustrates the preferred configuration of the cathode assembly.

In the preferred embodiment the cathode assembly may be the one shown in FIG. 4. Briefly, the cathode assembly comprises two or more cathodes. In the preferred embodiment shown in FIG. 4, the cathode assembly comprises three cathodes 5a, 5b, 5c. Preferably, the diameter of each cathode is 0.5 mm. The combined diameter of the three cathodes in the preferred embodiment is approximately 1 mm. At least one of the cathodes has a different length compared to other cathodes of the cathode assembly. Preferably, however, each cathode has a different length from all other cathodes in the assembly. The difference in length between two cathodes that have the closest lengths preferably equals to the cathode diameter, which is 0.5 mm in the preferred embodiment. The difference in length among the cathodes creates a natural surface imperfection to which the electric arc tends to attach.

In an alternative embodiment, a cathode assembly with a single cathode may be used, but such an embodiment is limited to certain applications that require a limited number of pulses. Cleaning of substrate surfaces with plasma pulses in microchip manufacturing is one such application. The embodiment of the device with the cathode assembly with a single cathode is suited to generate at most 300-500 pulses. After about 500 pulses, the temperature in the entire cathode body increases. This leads to an expansion of the area of contact between the plasma and the cathode surface when the arc is started. As a result, the plasma comes in contact with the cathode holder. Once the cathode holder begins to melt, it damages the cathode at the point where the cathode and the cathode holder are connected, creating an imperfection in that spot on the cathode. Once the imperfection is created the electric arc tends to attach to that imperfection, instead of the tip of the cathode, which disrupts the normal process of pulsed plasma generation and results in operational instability of the device. After the device cools down to room temperature, it is capable of generating another train of 300-500 pulses. Therefore, this alternative embodiment may be used for applications that require a limited number of pulses not exceeding approximately 500. The maximum number of pulses may be increased, but only insignificantly, by increasing the length of the cathode, thereby distancing the end of the cathode closest to the anode from the cathode holder.

Alternatively, to overcome the problem of operational instability of the embodiments of the device using a single cathode after a few hundred pulses, the cathode may be "trained" in the continuous plasma mode before switching to the pulsed plasma. Cathode training refers to the operation of the device in the continuous plasma mode, passing a high DC current through the cathode. Because initially, due to the geometry of the cathode and, in some embodiments the geometry of the plasma chamber, the electric arc attaches to the tip of the cathode, passing DC current through the tip of the cathode for a sufficiently long time creates a surface imperfection right at the tip of the cathode. After the cathode has been "trained," when the device is switched to the pulsed plasma mode, the electric arc attaches to the imperfection at the tip of the cathode that was created by the "training."

During operation, the plasma generating gas flows from console 100 to device 200. The plasma generating gas enters the device through passage 72. After the plasma generating gas passes cathode insulator 11, it passes through a plasma channel 62. This direction is referred to as the direction of the plasma flow. In the embodiments comprising a plasma chamber, the plasma generating gas passes plasma chamber 26 before it enters plasma channel 62. Plasma channel 62 is formed by anode 1 and two or more intermediate electrodes. The end of the plasma channel furthest from the cathodes is referred to as the anode end of the plasma channel; similarly the end of the plasma channel furthest from the anode is referred to as the cathode end of the plasma channel. Plasma channel 62 has an outlet at the anode end. In the embodiment shown in FIG. 2A, plasma channel 62 is formed by anode 1 and intermediate electrodes 2, 3, and 4. Intermediate electrode 4 also forms plasma chamber 26. In other embodiments, the electrode that forms plasma chamber 26 does not form a portion of plasma channel 62. Insulators 14, 13, and 12 provide electrical insulation between pairs of adjacent electrodes. Insulator 14 provides electrical insulation between the anode 1 and intermediate electrode 2; insulator 13 provides electrical insulation between intermediate electrodes 2 and 3; and insulator 12 provides electrical insulation between intermediate electrodes 3 and 4. Principles of plasma generation using a multi-electrode system are well known in the art.

Figure 2B:
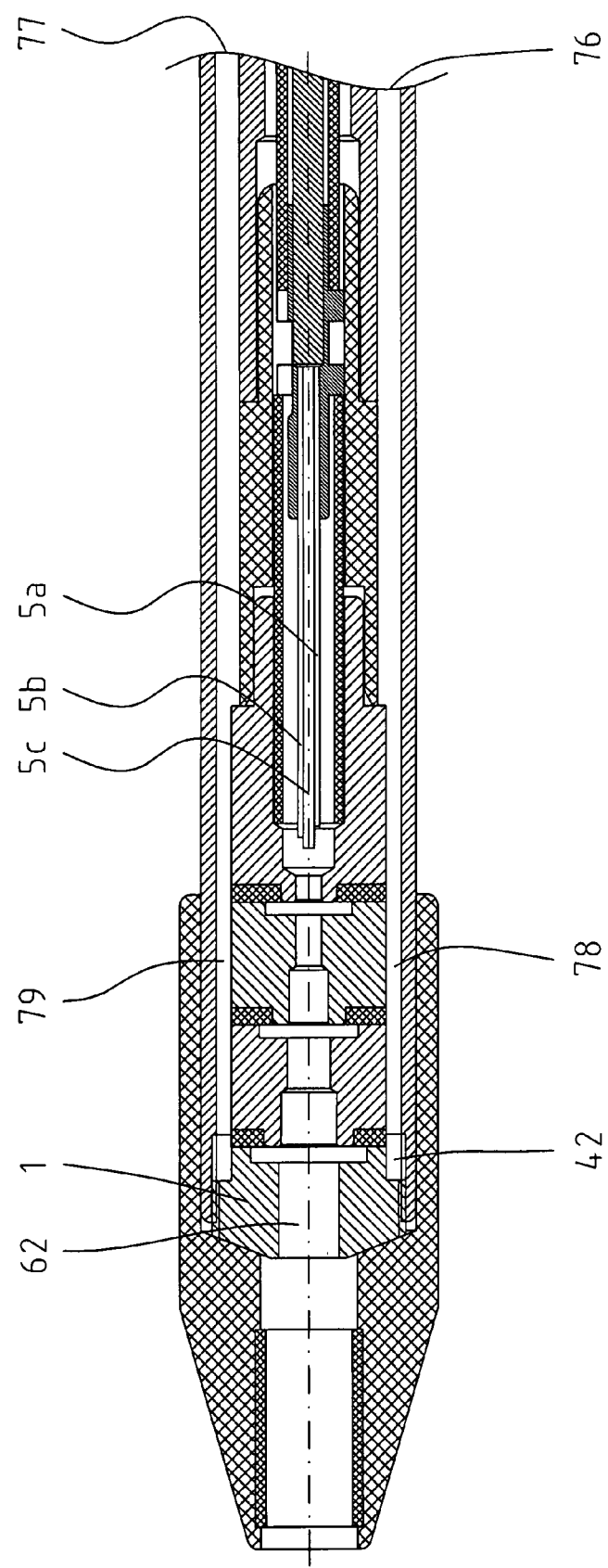
FIG. 2B illustrates a cross sectional longitudinal view, transversely to the view illustrated in FIG. 2A.

FIG. 2B shows a longitudinal cross section transverse to the cross section shown in FIG. 2A of the embodiment of device 200 shown in FIG. 1. FIG. 2B shows a cooling system comprising inlet 76, forward coolant channel 78, circular cooling channel 42 (shown in FIG. 2A), reverse coolant channel 79, and outlet 77. A coolant, preferably water, enters the device through inlet 76. The coolant then traverses forward coolant channel 78 along plasma channel 62 in the direction of the plasma flow, from cathodes 5a, 5b, 5c to anode 1. In the area of anode 1, forward coolant channel 78 connects to circular channel 42, shown in FIG. 2A. The coolant flows along circular channel 42 around anode 1. On the diametrically opposite side of the device, circular channel 42 connects to reverse coolant channel 79. The coolant flows along reverse coolant channel 79 in the direction opposite to the plasma flow, from anode 1 to cathodes 5a, 5b, 5c, and then exits the device through outlet 77.

Figure 3:
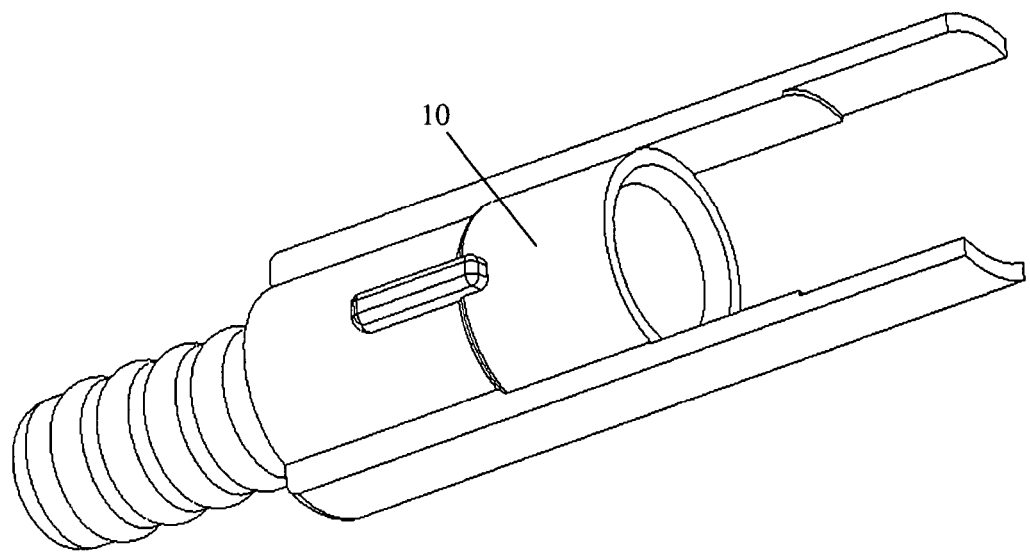
FIG. 3 illustrates a coolant divider.

FIG. 3 shows a coolant divider 10, which together with other elements forms forward coolant channel 78, circular channel 42, and reverse coolant channel 79. Some embodiments of the device may comprise multiple cooling systems. Such embodiments also comprise multiple coolant dividers that would form the respective channels of other cooling systems.

Figure 5:
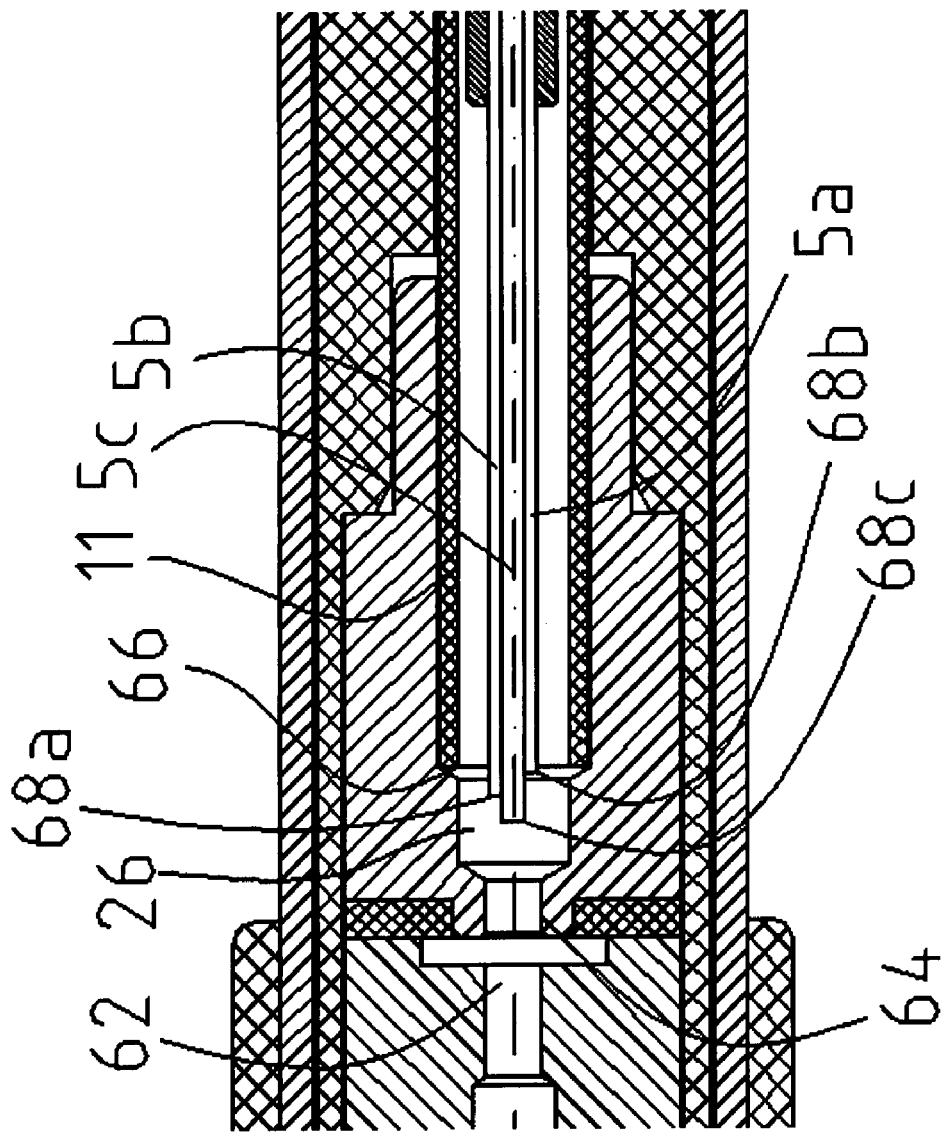
FIG. 5 illustrates the geometry of the plasma chamber.

If device 200 is subject to size constraints, such as for key hole surgeries, a plasma chamber may be used. FIG. 5 shows plasma chamber 26 in greater detail. The geometry of the plasma chamber 26 is critical to proper functionality of the device. Cathodes 5a, 5b, 5c tend to emit electrons from imperfections in their surfaces, for example their edges 68a, 68b, 68c, respectively. For proper operation, at the start of each pulse a spark discharge has to be established between one of cathode edges 68a, 68b, 68c and a point on the inside surface of plasma channel 62. To accomplish this, the following condition has to be satisfied. The distance between any of cathode edges 68a, 68b, 68c and a point on the inside surface of the plasma channel, for example point 64, must be less than or equal to the distance between any of cathode edges 68a, 68b, 68c and any other surface onto which an electric spark may terminate, such as the inside surface of plasma chamber 26 and the edge of the cathode insulator closest to anode 66. If the geometry of plasma chamber 26 and cathodes 5a, 5b, 5c shown in FIG. 5 is used, during the startup of the device, an electric spark occurs between cathodes 5a, 5b, 5c and a point on the inside surface of plasma channel 62, for example point 64. This ensures proper operation of the plasma generating process. This geometry of plasma chamber 26 also results in other benefits, such as decreasing the time required to achieve the arc discharge phase, which is critical for pulsed plasma, as described below. If device 200 is not subject to size constraints, which is the case for most skin treatment applications, the plasma chamber is optional.

Figure 6:
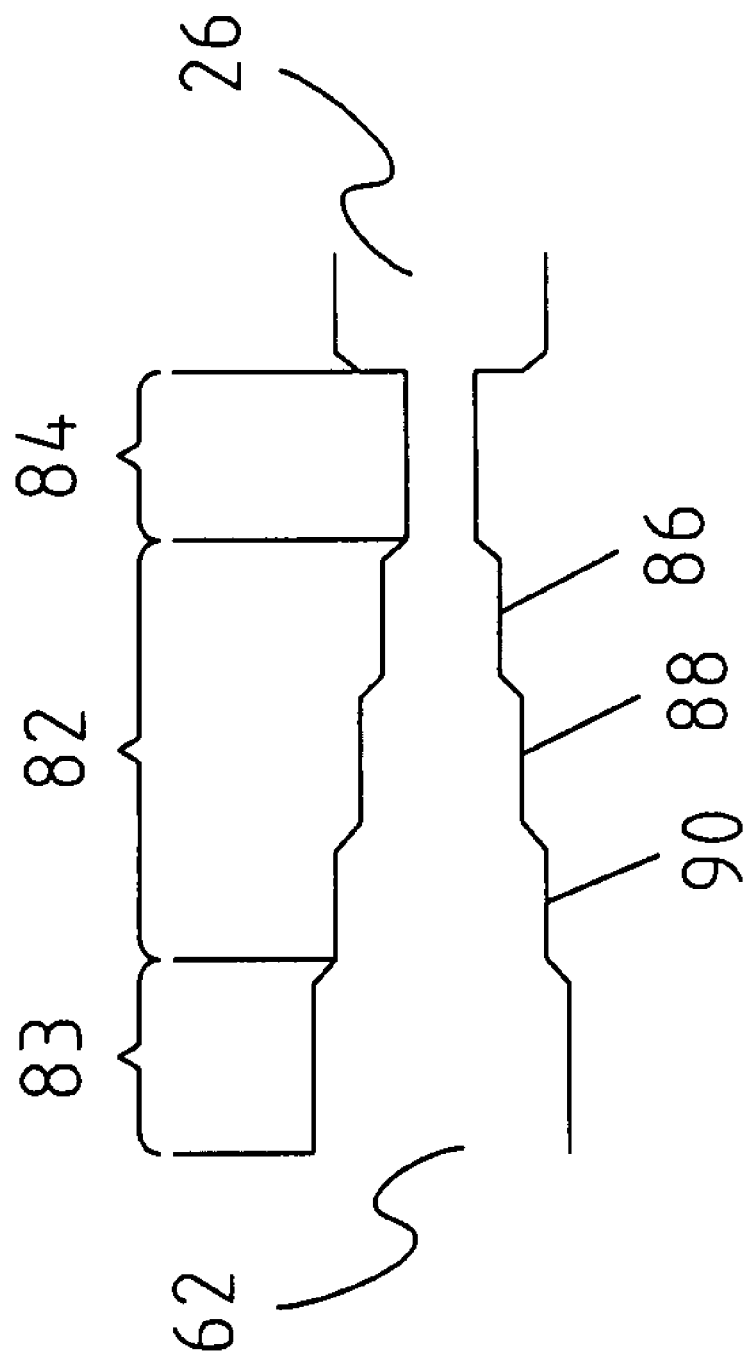
FIG. 6 illustrates a heating portion, an expansion portion, and an anode portion of the plasma channel and sections of the expansion portion.

FIG. 6 shows the structure of plasma channel 62. Plasma channel 62 comprises heating portion 84, expansion portion 82, and anode portion 83. Expansion portion 82 and anode portion 83 are used to expand the plasma flow to the required cross-sectional area for a given application. Expansion portion 82 comprises one or more expansion sections. In the embodiment shown in FIG. 6, expansion portion 82 comprises expansion sections 86, 88, and 90.

In the preferred embodiment, heating portion 84 is formed by two to five intermediate electrodes. In alternative embodiments, heating portion 84 may be formed by a single intermediate electrode or by six or more intermediate electrodes. The diameter of heating portion 84, $d_{hp}$, is preferably in the range of 0.5-1.5 mm. The length of each electrode forming heating portion 84, $l_{e\_hp}$, depends on $d_{hp}$ and is preferably in the range of $d_{hp}$ to $2 \times d_{hp}$. The length of the entire heating portion depends on the flow rate of the plasma generating gas—a longer heating portion is required to heat a greater plasma generating gas flow. For a typical flow rate of plasma generating gas, which is in the range of 1 to 2 l/min, the heating portion is formed by at least three intermediate electrodes. The length of the entire heating portion, $l_{hp}$, may be approximated by multiplying the number of intermediate electrodes that are required to form the heating portion by the length of such an intermediate electrode, $l_{e\_hp}$.

The number of sections in expansion portion 82 depends on the diameter of the heating portion 84 and the diameter of anode portion 83, and is governed by the following relationship:

$$N_s \geq \frac{d_A - d_{hp}}{c} - 1, \text{ where}$$

$N_s$ is a number of sections in the expansion portion of the plasma channel, $d_A$ is the diameter of the anode portion of the plasma channel in millimeters, $d_{hp}$ is a diameter of the heating portion of the plasma channel in millimeters, and c, for this and other equations, is a constant in the rage between 0.2-0.6 mm, preferably 0.4 mm. Although c may be chosen to be less than 0.2, as will be shown below, choosing such value of c results in an impracticable length of device 200.

For the purposes of this disclosure, the sections of expansion portion 82 are counted from cathodes 5a, 5b, 5c toward the anode 1. So that section 86 is section no. 1; section 88 is section no. 2; section 90 is section no. 3, etc. If a particular embodiment has more than three sections they are counted in this manner as well. The dimensions of the sections of expansion portion 82 are preferably governed by the following relationships:

$d_n$ is preferably $d_{n-1}+c$, $l_n$ is preferably between $d_n$ and $2 \times d_n$, where n is the section number of a given section, $d_n$ is the diameter of the nth section, and $l_n$ is the length of the nth section.

For determining the diameter of section no. 1, section 86 in FIG. 5, the value of $d_0$, required to compute $d_1$, is set to the diameter of the heating portion, $d_{hp}$.

The dimensions of anode portion 83 are preferably governed by the following relationships:

$d_A$ is preferably $d_z+c$, $l_A$ is preferably between $2 \times d_A$ and $5 \times d_A$, where $d_A$ is a diameter of the anode portion, $l_A$ is a length of the anode portion, and z is the number of expansion section of expansion portion 82 closest to the anode. In FIG. 6, z is 3, which is the number of expansion section 90.

In the preferred embodiment, cross-sections of the plasma channel transverse to the longitudinal direction of the plasma channel are circles. In other embodiments, however, cross-sections may have a different geometric shape.

In some embodiments of the device, each section of the expansion portion is formed by a separate intermediate electrode. In other embodiments of the device, a single intermediate electrode may form portions of two or more adjacent sections. In yet some other embodiments, some intermediate electrodes may form a portion of a section, or an entire section, of the expansion portion, and other intermediate electrodes may form only portions of two or more adjacent sections. In the embodiment shown in FIG. 2A, intermediate electrode 3 forms section 86 (and heating portion 84), and intermediate electrode 2 forms sections 88 and 90.

Figure 2C:
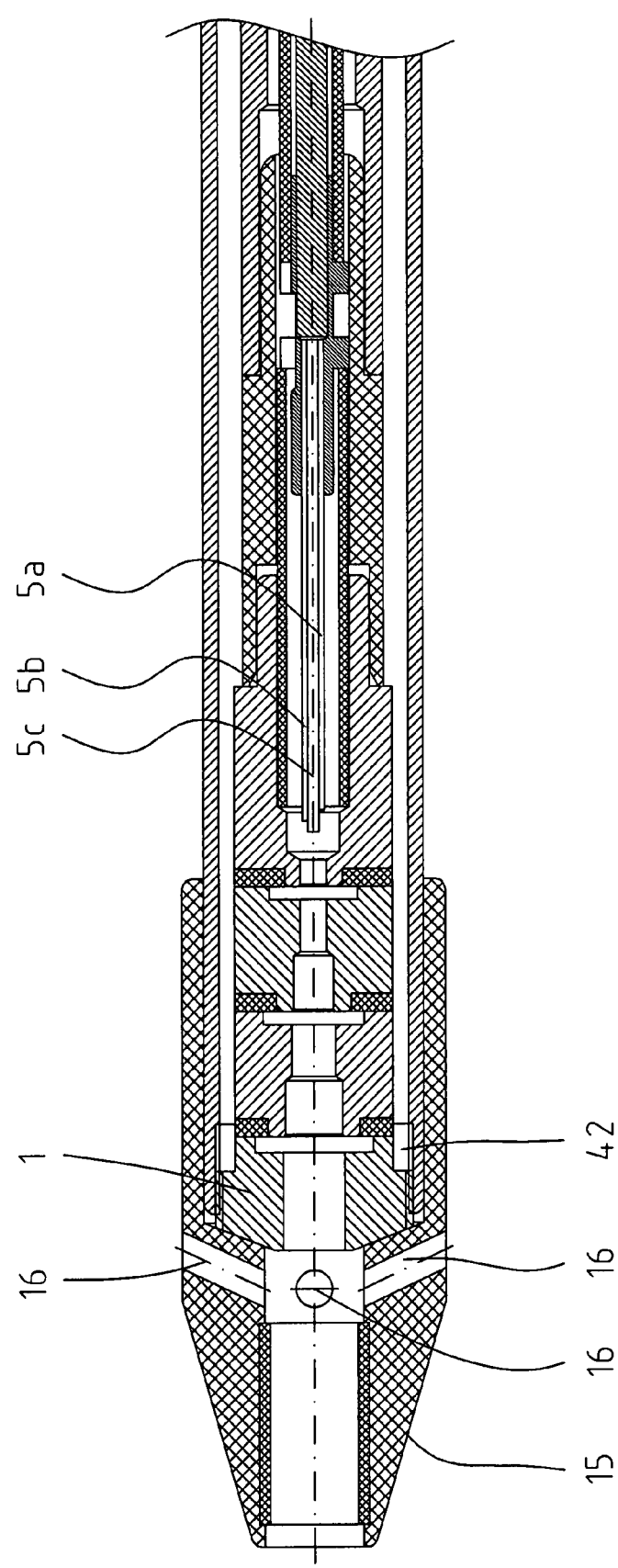
FIG. 2C illustrates a cross sectional longitudinal view of an embodiment of the device configured to generate ozone.

Device 200 includes an extension nozzle. For example, turning back to FIG. 2A, extension nozzle 15 is affixed to the anode end of the device. Extension nozzle 15 has extension channel 18, which extends the plasma channel. A portion of the extension channel 18 is formed by tubular insulator element 17 made of a ceramic material or quartz. Tubular insulator element 17 prevents the termination of an electric discharge in extension nozzle 15. That, in turn, prevents electrode materials from separating from extension nozzle 15 and entering the plasma flow during operation of device 200. This ensures the purity of the plasma exiting an extension channel from outlet 55. The diameter of the portion of extension channel 18 formed by tubular insulator element 17 is preferably in the range of 1.0-1.3 times the diameter of anode portion 83 of plasma channel 62. The length of extension channel 18 is preferably 2-3 times its diameter. In those embodiments that are configured for generation of ozone, extension nozzle 15 also has one or more oxygen carrying gas inlets 16 as shown in FIG. 2C. Inlets 16 are used for supplying oxygen carrying gas, preferably air, to extension channel 18, which may be used for production of ozone, as described below.

The computations of dimensions of different elements in the preferred embodiment of the device are illustrated by the following example. Assume the heating portion has a diameter of 1.0 mm and a length of 1.5 mm (which are governed largely by the flow rate of the plasma generating gas) and the desired diameter of the plasma flow exiting the device from the outlet of extension channel 55 is 4.8 mm. The diameter of the extension channel would be 4.8 mm and its length may be set to any length in the range of 2-3 times its diameter, for example 14.0 mm. The diameter of the extension channel should be 1.0-1.3 times the diameter of the anode portion of the plasma channel, and is preferably between 6 mm and 12 mm. In this example, if the diameter of the extension channel is 1.2 times the diameter of the anode portion of the plasma channel, the diameter of the anode would be 4.0 mm. The length of the anode portion may be any length between 2 times its diameter and 5 times its diameter. In this example, when the length of the anode is set to 3 times its diameter, the length would be 12.0 mm. The expansion portion expands the diameter of the plasma channel from the diameter of heating portion 84, which in this example is 1.0 mm, to the diameter of the anode portion of the plasma channel, which is 4.0 mm. Accordingly, in this example the expansion portion expands the diameter of the plasma channel by 3.0 mm. This expansion may be accomplished in a number of ways. For example, diameters of each section of the expansion portion may increase by the maximum c of 0.6 mm. In this case, the number of sections in the expansion portion, $N_s$ is 4. The diameters of these sections are as follows: 1.6 mm, 2.2 mm, 2.8 mm, and 3.4 mm. The lengths of the sections may be set to any values between one and two times the diameter. Accordingly, the length of the sections may be: 2.0 mm, 3.0 mm, 4.0 mm, and 5.0 mm, respectively. If the diameter increase of each section is chosen to be less than 0.6 mm, then more sections in the expansion portion are needed.

Alternatively, c may be set to the preferred value of 0.4 mm. In this case, the number of sections in the expansion portion, $N_s$, is 7. The diameters of these sections are as follows: 1.4 mm, 1.8 mm, 2.2 mm, 2.6 mm, 3.0 mm, 3.4 mm, and 3.8 mm. The lengths of the sections may be 3.5 mm, 4.5 mm, 5.5 mm, 6.5 mm, 7.5 mm, 8.5 mm, and 9.5 mm, respectively. Note that in this example, the expansion between the expansion section closest to the anode and the anode is only 0.2 mm, as opposed to 0.4 mm. This does not impair the functionality of the device.

It is further possible to have a different expansion between different pairs of sections of the expansion portion. For example, the expansion from the heating portion to the first section may be 0.4 mm, and the expansion between other expansion sections and the anode may be 0.5 mm.

The above discussion presumes that the intermediate electrodes, the anode, and the extension nozzle are annular, thus making the portions and sections of the plasma channel and the extension channel cylindrical. As mentioned above, in some embodiments other geometry of the device may be used. In those embodiments, the diameter of the cross section transverse to the longitudinal direction of the plasma channel, which, for the purposes of this disclosure is the largest distance between any two points of a shape, remains the critical dimension for purposes of the foregoing calculations.

Figure 7A:
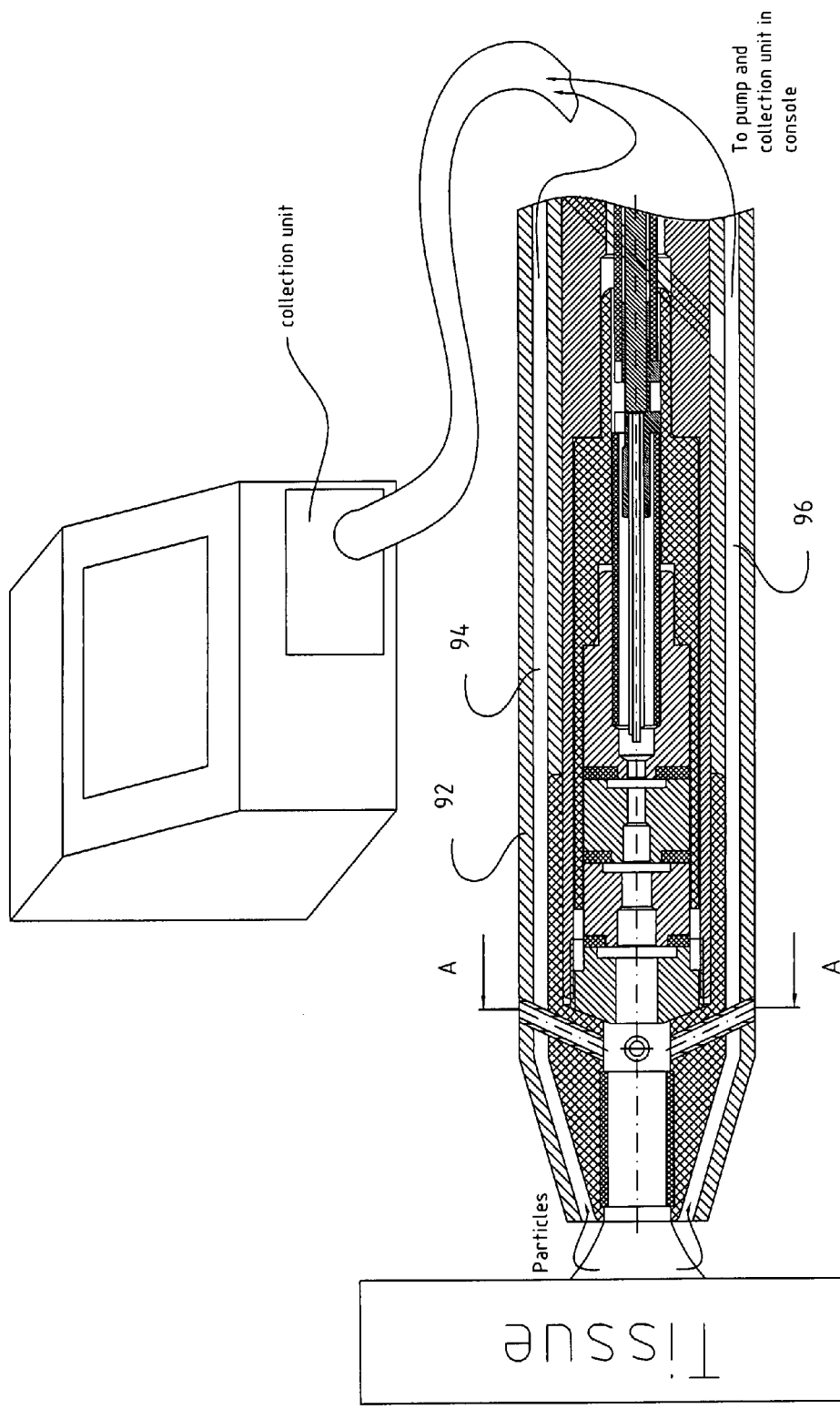
FIG. 7A illustrates an embodiment of the device comprising a suction module in which extraneous matter is collected in the console.
Figure 7B:
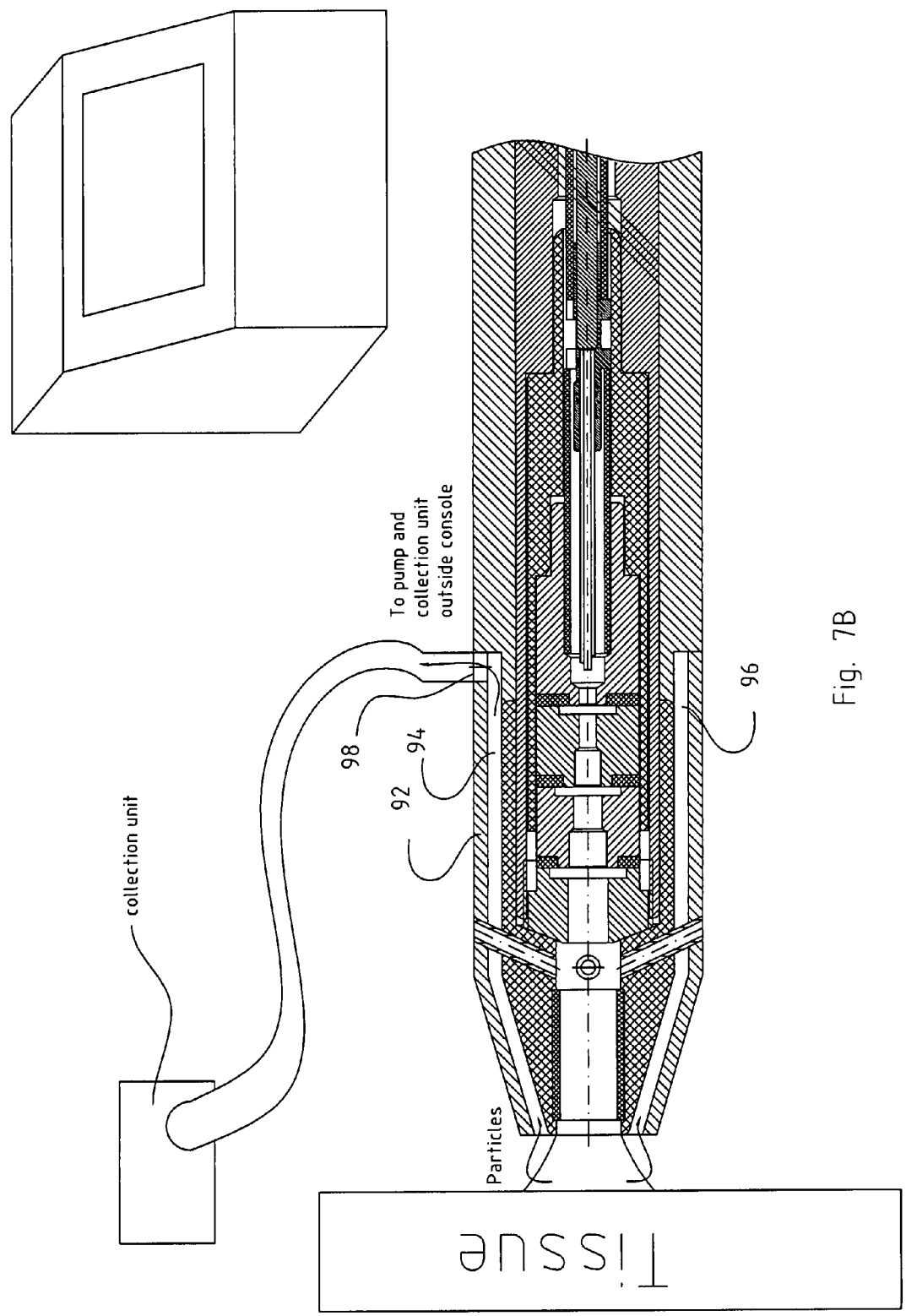
FIG. 7B illustrates an embodiment of the device comprising a suction module in which extraneous matter is collected in an outside container.
Figure 7D:
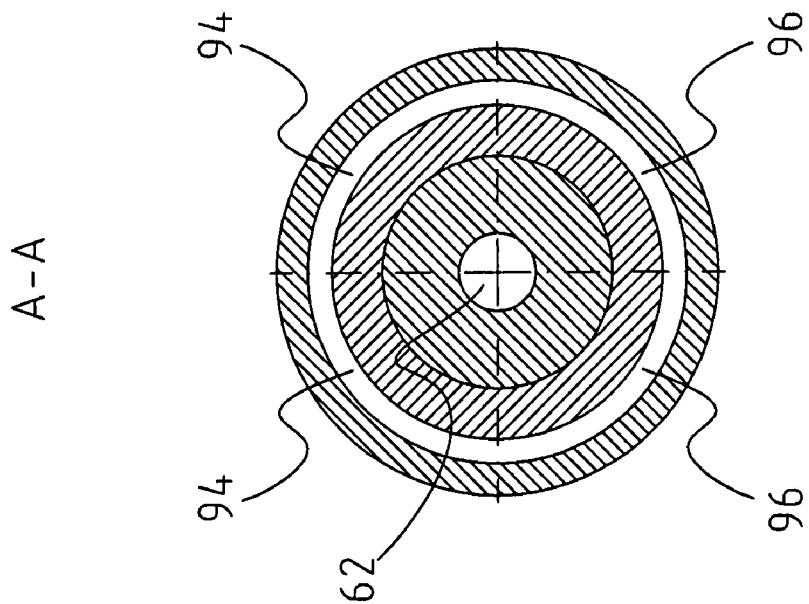
FIG. 7D illustrates a cross sectional view of an embodiment of the device comprising an extension nozzle without oxygen carrying gas inlets and a suction module.
Figure 7C:
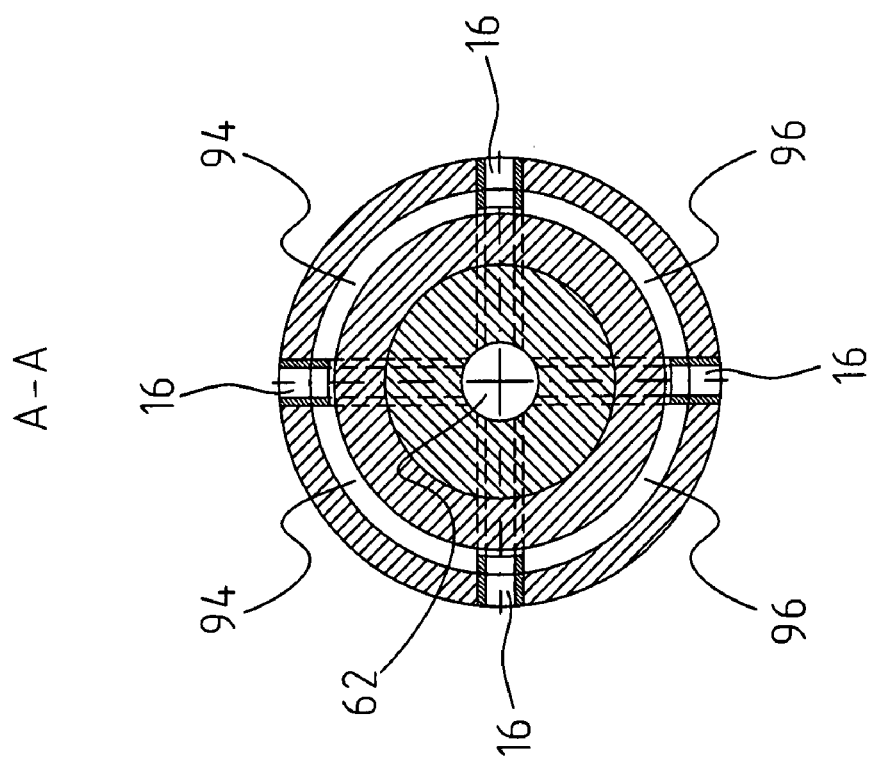
FIG. 7C illustrates a cross sectional view of an embodiment of the device comprising an extension nozzle with oxygen carrying gas inlets and a suction module.

As mentioned above, when plasma is used to perform medical procedures, extraneous matter, that may attenuate the effect of the plasma, may be created. For example, during a medical procedure, particles or pieces may separate from the treated tissue, and then interfere with, or even interrupt, the plasma flow to the target area of the treated tissue. Also, during certain medical procedures bodily fluids, such as blood, lymph, etc. may enter onto the surface of the treated area. Those fluids may also interfere with the effectiveness of plasma. Some embodiments of the device include a suction module for removing such extraneous matter from the treated surface during medical procedures. FIG. 7A shows an embodiment of the device with a suction module. In this embodiment, outer casing 92 encloses the device shown in FIGS. 2A-C. Outer casing 92 has one or more suction channels 94, 96. A pump operating inside console 100 sucks the extraneous matter from the treated tissue. The extraneous matter flows along channels 94 and 96, and then to console 100, where it is accumulated in a collection unit (not shown in FIG. 7A). FIG. 7B shows a different embodiment of the device with a suction module. This embodiment is similar to the embodiment shown in FIG. 7A except that channels 94 and 96 do not extend along the partial length of the device and are connected with outlet 98. Note that in embodiments that include both a suction module and an extension nozzle with oxygen carrying gas inlets, the inlets extend through casing 92 as illustrated in FIG. 7C that shows cross section A-A in FIG. 7A. FIG. 7D shows cross section A-A in embodiments comprising an extension nozzle without oxygen carrying gas inlets.

In the preferred embodiment the device generates truly pulsed plasma. After each plasma pulse, during the off period, the flow of plasma completely ceases until the next pulse. Between the pulses, during the off period, the electric current does not flow between the cathode and the anode and no plasma is generated.

Console 100 has one or more electronic circuits for controlling the current through the plasma channel and applying the voltage between the cathode and the anode. These circuits are used for generation of each plasma pulse. As a brief overview, the process of plasma generation includes three phases: a spark discharge, a glow discharge, and an arc discharge. During the arc discharge phase, an electric arc of a predetermined current that is established between one of the cathodes and the anode, heats the plasma generating gas flowing in plasma channel 62 and forms plasma. Generation of each plasma pulse requires the plasma generating gas to go through all three phases. Prior to generation of a pulse, the resistance of the plasma generating gas is close to infinity. A small number of free electrons are present in the plasma generating gas due to ionization of atoms by cosmic rays. The plasma formation process is controlled by (1) applying the voltage applied between the cathode and the anode as shown in FIG. 8A and (2) controlling the current passing through the plasma as shown in FIG. 8B.

The method of operating the device depends on the structure of the cathode assembly and may be modified depending on the configuration of the device and a particular application for which it is used. In the preferred embodiment of the device having a cathode assembly comprising multiple cathodes, a method of operation specifically adapted for the cathode assembly shown in FIG. 4 is used. Briefly, to create a spark discharge a high amplitude, high frequency voltage wave is applied between anode 1 and cathodes 5a, 5b, 5c. This wave increases the number of free electrons in plasma channel 62, between cathodes 5a, 5b, 5c and anode 1. The frequency, duration, and amplitude of the wave depends on the geometry of the device. Once a sufficient number of free electrons has been formed, a DC voltage is applied between anode 1 and cathodes 5a, 5b, 5c and a DC current is passed through the cathodes, plasma generating gas, and the anode, forming a spark discharge between cathodes 5a, 5b, 5c and anode 1.

Thereafter the resistance of the plasma generating gas drops and the glow discharge phase begins. During the glow discharge phase, positively charged ions, formed as a result of ionization, are attracted to the cathode under the influence of the electric field created by the voltage between cathodes 5a, 5b, 5c and anode 1. As cathodes 5a, 5b, 5c are being bombarded with ions, the temperature of the cathode ends closest to anode 1 increases. Once the temperature increases to the temperature of thermionic electron emission, the arc discharge phase begins. As mentioned above, the surface area and volume of plasma chamber 26 provide a large number of ions, which shortens the time of the glow discharge phase.

Once the arc discharge begins, the plasma is attached to all cathodes in the assembly. The current passing through the plasma is then dropped, causing the area of attachment to decrease to almost the minimum area of attachment capable of sustaining the arc discharge. This minimal area is referred to as the spot attachment area. Because the area of plasma attachment is small, the attachment occurs only at a single cathode. Therefore, the current required to sustain the arc discharge, which is proportional to the cathodes diameter, is relatively low. After the current has been reduced and kept at the level for a period of time, it is increased rapidly to the operational level of a pulse. The area of attachment of plasma increases insignificantly, and only a single cathode continues to emit electrons for the rest of the pulse. Decreasing the area of plasma attachment, and then maintaining the small area, so that only a single cathode emits electrons from a controlled area is critical to the operation of the device.

As mentioned above, in different embodiments, variations of this method of operation may be used. For example, in the alternative embodiment with a single cathode, the area of attachment may only be controlled with the length of the cathode and tapering of the cathode end or cathode training. In those embodiments, the current is increased to the operational level as soon as the arc discharge phase is reached.

The geometry of elements in the disclosed embodiments and the shape and synchronization of the voltage and current pulses ensure that the cathodes (or the cathode, depending on the embodiment) are not subjected to the stress of high current being passed through it when there is no thermionic electron emission sufficient to support the current. That in turn ensures that the device may be started thousands or even tens of thousands times with the same cathode assembly.

The relationships governing the dimensions of different sections in the expansion portion allow the plasma to expand rapidly, during the operational period of the pulse, which is critical for generating a pulse of plasma with required characteristics. It has been experimentally found that a single increase in the diameter of the plasma channel by more than 0.6 mm results in incomplete plasma flow expansion, or even no expansion at all, during the operational period of the pulse. In other words, if the diameter of an nth section of the expansion portion is increased by more than 0.6 mm compared to the diameter of the (n−1)th section, the plasma flow does not expand to the diameter of the nth section, and the plasma flow is restricted to a particular cross-section that is smaller than the cross section of the nth section while it traverses the remaining downstream portion of the plasma channel and the extension channel. FIG. 9 illustrates this concept. In FIG. 9, there is no expansion portion 82. The heating portion 84a transitions into anode portion 83a. The diameter of the anode portion 83a exceeds the diameter of the heating portion 84a by more than 0.6 mm. The plasma flowing in plasma channel 62a does not expand, or expands insufficiently, during the operational period of the pulse, when the plasma enters the anode portion 83a. A very similar situation occurs when there is an expansion portion, but the difference in the diameter between adjacent sections exceeds 0.6 mm. However, when the dimensions of the expansion sections are within the ranges governed by the relationships set forth above, the plasma flow expands to the entire cross-section at the anode end of each section, so that the diameter of the plasma flow equals the diameter of the extension channel at the outlet 55. Note that for longer pulses or continuous plasma flow, increases of 0.6 mm and above may result in partially expanded plasma flow. Essentially, for brief pulses required for such applications as skin treatment, a single diameter increase has to be less than or equal to 0.6 mm so that the plasma flow fully expands to the increased diameter in each section.

Another problem presented by a single diameter increase of more than 0.6 mm is the potential for the formation of an electric arc between the plasma flow and a wall of the anode, if the plasma flow is separated from the wall. This is also shown in FIG. 9. FIG. 9 shows electric arc 171 formed between the plasma flow and the wall of the anode 1. Such an electric arc would introduce electrode materials into the plasma flow and would make the plasma impure. This process of gradual widening of the plasma flow plays a major role in generating a truly pulsed plasma flow, when the current in the arc rapidly increases while the plasma in the flow has not been heated sufficiently.

Increasing the diameter of the plasma channel by less than 0.2 mm results in neither impurities nor insufficient expansion of plasma. However, expansion of less than 0.2 mm is also undesirable. In particular, a device with expansions of less than 0.2 mm would require a greater number of expansion sections. Each expansion section has its minimal length requirements, so having a greater number of expansion sections means having a longer and less convenient device. Additionally, aside from mere inconvenience, an increased number of expansion sections requires more energy and therefore greater power for heating the plasma flow that traverses a plasma channel the length of which is increased due to the increased number of the expansion sections. Accordingly, although the device would function properly even with increases of section diameters of less than 0.2 mm, it is preferable that each expansion is within the range of 0.2-0.6 mm.

Figure 8C:
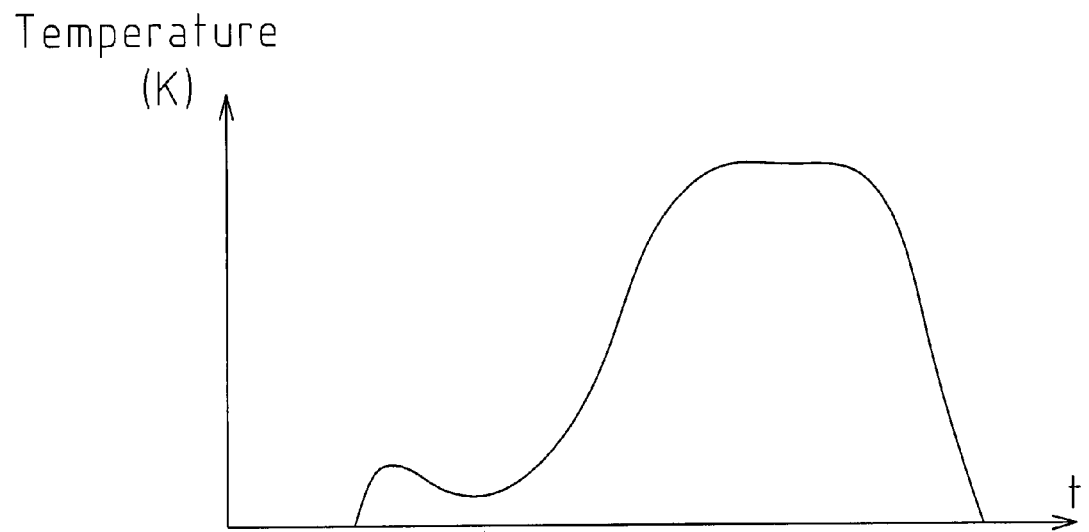
FIG. 8C illustrates the temperature profile of the plasma in the heating portion of the plasma channel.
Figure 8D:
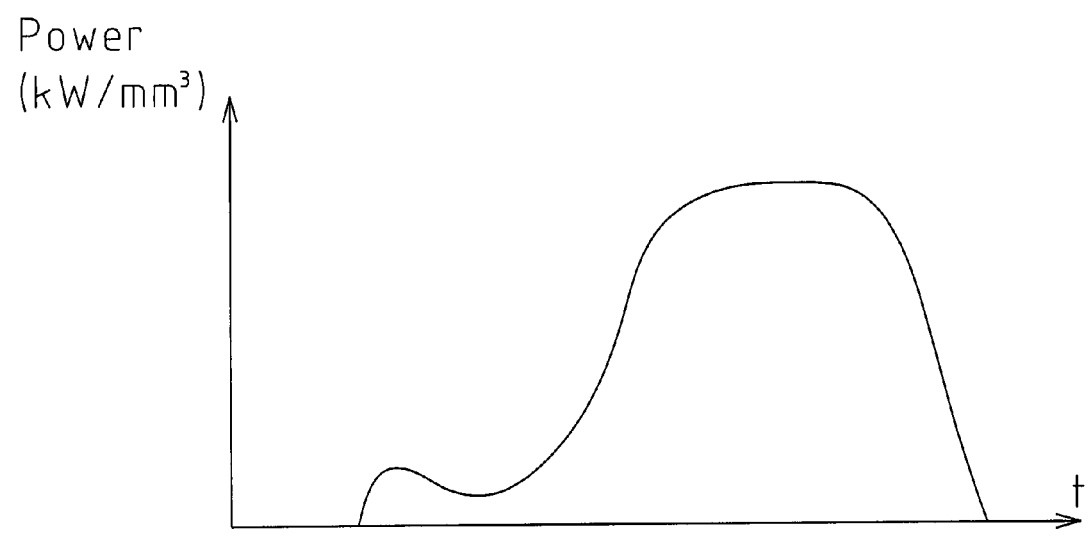
FIG. 8D illustrates the power density profile of the plasma in the heating portion of the plasma channel.

As the plasma expands in expansion portion 82, some of its properties change. During the operational period of the pulse, the heating portion is characterized by a power density in the range of 0.3-5 kW/mm$^3$, as shown in FIG. 8D. The average velocity of the plasma flow in the heating portion is preferably less than or equal to 500 m/s. The average temperature of the plasma is 8-18° kK, preferably 10-16° kK, as shown in FIG. 8C. The electric field in the heating portion is preferably in the range of 2-25 V/mm.

The expansion portion is characterized by a power density of less than 0.3 kW/mm$^3$. The average temperature of the plasma in the expansion portion preferably remains in the range of 8-18° kK. The electric field in the expansion portion of the plasma channel is preferably within a range of 1-5 V/mm.

After the plasma flow expands in expansion portion of the plasma channel 82, it reaches extension nozzle 15. Extension nozzle 15 has a dual effect on plasma flow: first it changes the temperature and energy distribution of the plasma flow to make it suitable for a particular application, such as tissue treatment and second, it may create ozone and nitric oxide in the plasma flow.

Figure 10:
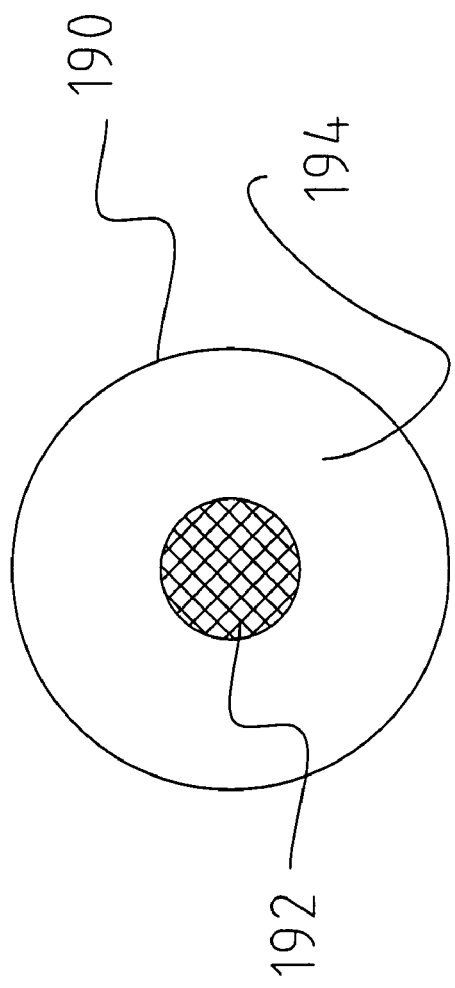
FIG. 10A illustrates a substantially parabolic temperature and power density distribution of the plasma flow exiting the anode.
FIG. 10B illustrates the effect on a tissue when treated with the plasma flow having the temperature and power density distribution illustrated in FIG. 10A.
Figure 10:
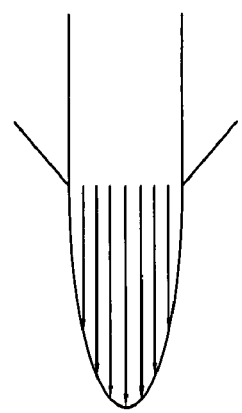

The first effect of extension nozzle 15 on the plasma flow is changing the temperature and energy distribution of the plasma flow. During the arc discharge phase, the electric arc between the cathode and the anode heats the plasma in plasma channel 62. Only a small fraction of the plasma forms the center of the plasma flow where the temperature is high. The remaining plasma flows along the periphery of the plasma channel at a distance from the electric arc, and therefore has a substantially lower temperature. The plasma flowing along the periphery of the plasma channel cannot be heated to the same temperature as the plasma flowing in the center because the intermediate electrodes and the anode forming the plasma channel are made of metals with a high thermal conductivity. Accordingly, the heat transferred from the plasma flowing in the center to the plasma flowing along the periphery is transferred to the intermediate electrodes and the anode and is not retained by the plasma flowing along the periphery. When the plasma reaches the anode end of plasma channel 62, it has a substantially parabolic temperature distribution as shown in FIG. 10A. As illustrated in FIG. 10A, the temperature of the plasma in the center of the plasma flow is substantially higher than the temperature at the periphery of the plasma flow. Similarly the energy density of the plasma, which is proportional to the temperature, is substantially higher in the center of the plasma flow than at the periphery.

Such temperature and energy density distribution of the plasma flow is not suitable for some applications, such as skin treatment. When a pulse of plasma flow with such temperature and energy density distribution comes in contact with the skin of a patient, a small area of the skin absorbs most of the energy in the plasma flow pulse, and a much larger area absorbs the remainder of the energy. FIG. 10B shows circular area 190 of the skin having the diameter of the plasma channel in the anode portion. If a pulse of plasma flow as shown in FIG. 10A comes in contact with area 190, an approximately 20% fraction 192 of area 190 absorbs approximately 80% of the energy stored in the plasma pulse. The remaining 80% fraction 194 of area 190 absorbs only about 20% of the energy stored in the plasma pulse.

Figure 11:
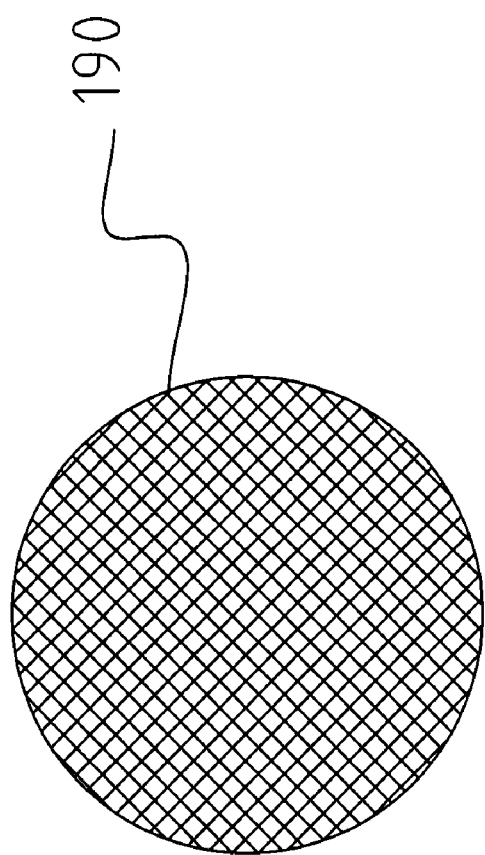
FIG. 11A illustrates a substantially uniform temperature and power density distribution of the plasma flow exiting the extension nozzle.
FIG. 11B illustrates the effect on a tissue when treated with the plasma flow having the temperature and power density distribution illustrated in FIG. 11A.
Figure 11:
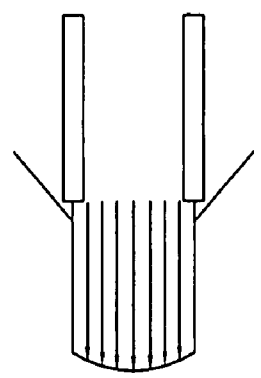

The extension nozzle changes the temperature and energy density distribution to a substantially uniform one as illustrated in FIG. 11A. In other words, the temperature and energy density of the plasma flow that exits the extension nozzle from outlet 55 is approximately the same in the entire cross section of the flow. FIG. 11B illustrates an area of skin treated with a plasma flow having the distribution shown in FIG. 11A. As shown in FIG. 11B, when a pulse of plasma flow comes in contact with the skin, the entire area is affected by the pulse substantially uniformly, and there are no spots that receive substantially more or substantially less energy. In the preferred embodiment, the geometry of the elements in the device as well as operational parameters (i.e. plasma generating gas flow rate, magnitude of the current, etc.) are selected in such a way that the energy density of the plasma applied to the treated tissues is 5-500 $J/cm^2$. In other embodiments, other energy density may be achieved.

As mentioned above, when the plasma exits the anode and enters the extension channel, its temperature and energy density have a parabolic distribution as shown in FIG. 10A. One of the main reasons that the plasma flow does not achieve uniform temperature in the plasma channel is that intermediate electrodes and the anode are made of metal, such as copper, having a high thermal conductivity. Due to the high thermal conductivity, the heat from the plasma is transferred to the coolant flowing along channels 78 and 79. Anode 1 and the intermediate electrodes intensively cool the periphery of the plasma, thus forming a large temperature gradient. Insulator element 17 located in extension channel 18, is preferably made of quartz or a ceramic material that has a very low thermal conductivity. Accordingly, when the heated plasma comes in contact with insulator element 17 that does not cool plasma, the heat is not distributed through the entire volume of insulator element 17. Only the inside surface of the insulator element 17 that comes in contact with the heated plasma is rapidly heated to the temperature of the plasma and is not cooled down. Because there is minimal heat dissipation to the extension nozzle, the temperature of the plasma flowing along the periphery increases. As the heat is transferred from the center of the flow to the periphery, the heat is not transferred to the structural elements of the device. Also, in extension channel 18 the center of the plasma flow is not heated by the electric arc, which terminates at the anode. Accordingly, when the plasma flow exits extension channel outlet 55, it has a substantially uniform temperature and energy density distribution as shown in FIG. 11A. FIG. 11B shows that the substantially uniform temperature and energy density distribution results in the substantially uniform effect by the plasma on the treated tissue.

The second, optional, effect of the extension nozzle is generating ozone and nitric oxide. In some countries it has been recognized that ozone exhibits properties useful in medicine such as, for example, an antibacterial effect. In other countries, however, the benefits of ozone have not been recognized. It is well known in the art, however, that ozone may be formed from oxygen by electrical discharges, high temperature, and exposure to high energy electromagnetic radiation. When $O_2$ molecules are introduced in the plasma flow, some of them are disassociated into oxygen atoms under the influence of one or more of the above conditions, and then recombine with $O_2$ molecules to form ozone ($O_3$).

Figure 12B:
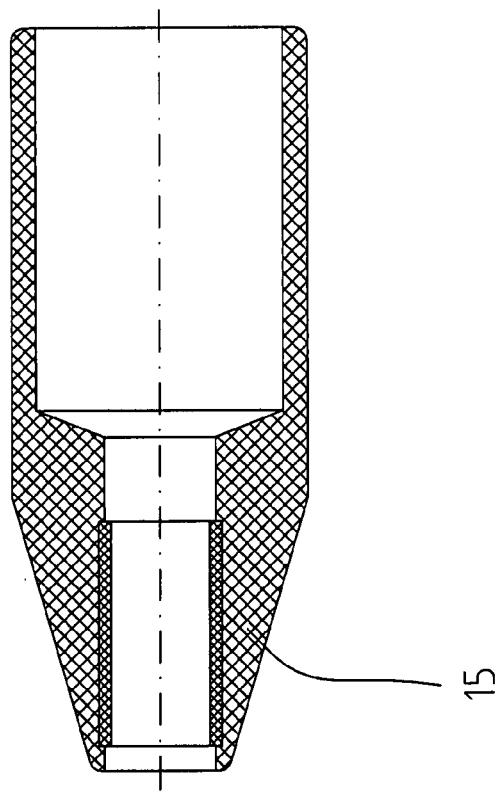
FIG. 12B illustrates an extension nozzle having no oxygen carrying gas inlets.
Figure 12A:
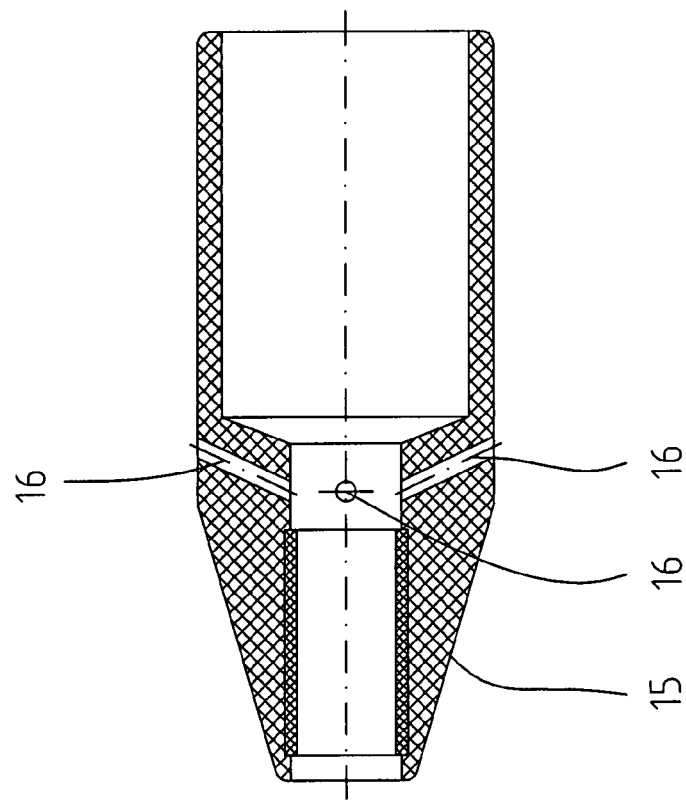
FIG. 12A illustrates an extension nozzle having oxygen carrying gas inlets of a relatively small diameter.

In some embodiments, the device generates ozone, while in other embodiments, the device does not generate ozone. Generation of ozone may be controlled in two ways. First, the inlet of oxygen carrying gas may be controlled by reducing the diameter, or even completely eliminating oxygen carrying gas inlets. FIG. 12A illustrates extension nozzle 15 with inlets 16 of relatively small diameter. FIG. 12B illustrates extension nozzle 15 having no oxygen carrying inlets at all. Second, the length of the extension channel 18 can be reduced so that oxygen entering through the inlets does not have time to undergo the reactions required to generate ozone. It should be understood that by using one or both of these ways of controlling generation of ozone, the amount of ozone generated by device 200 may be increased, reduced, or even completely eliminated. Similarly, generation of nitric oxide is controlled the same ways. The following discussion related to generation of ozone and nitric oxide presumes that extension nozzle 15 has one or more oxygen and nitrogen carrying gas inlets 16.

Turning to the processes that result in generation of ozone, the plasma flow, after having traversed the plasma channel, enters extension nozzle 15. The temperature of the plasma flow in the extension channel drops preferably to 3-12° kK. During operation, as the plasma flows by oxygen carrying gas inlets 16, it creates a suction effect in those inlets 16, which results in an oxygen carrying gas, such as air, being pulled into extension channel 18. In the extension channel, the fraction of air is preferably in the range of 5-25%, by volume. It is well known that air contains approximately 21% of $O_2$ oxygen by volume, and therefore, the fraction of $O_2$ in the extension channel is preferably in the range of 1-5%, by volume. Some oxygen molecules will disassociate into atoms and then recombine with $O_2$ oxygen molecules, or sometimes with other disassociated oxygen atoms, to form ozone under the influence of two factors: (1) impacts of $O_2$ molecules with electrons that have a relatively high energy and (2) the ultraviolet radiation from the plasma channel due to the emission of plasma generating gas molecules, electrons, and other particles. The formation of the ozone molecules occurs in accordance with the following chemical reactions:

$$e + O_2 \rightarrow O + O^{31};$$

$$e + O_2 \rightarrow O + O + e; \text{ and}$$

$$O + O_2 + M \rightarrow O_3 + M,$$

where M may be any reacting particle, such as a molecule of a noble gas, for example argon.

Another effect of introducing an oxygen and nitrogen carrying gas into the plasma flow is generation nitric oxide (NO) in extension channel 18. Various therapeutic effects of NO and methods of its generation are well known in the art and are recognized in some countries. For example, U.S. Pat. No. 5,396,882 discloses systems and methods for producing NO by introducing air into electric arc chamber. Embodiments of the device having an expansion module, likewise, create conditions for producing NO. Introducing a nitrogen and oxygen carrying gas, such as air, into the plasma flow creates optimal conditions for the synthesis of NO in the expansion channel 18. As was mentioned above the temperature of the plasma at the anode outlet is in the range of 3°-12° kK. This temperature is sufficiently high for the following chemical reaction to occur in the plasma flow having air molecules, concurrently with the ozone production:

$$N_2 + O_2 \rightarrow 2NO - 180.9 kJ.$$

In some embodiments, the fraction of air, oxygen or both may be varied. For example, in some embodiments, air enriched with oxygen may be supplied to the oxygen carrying gas inlets 16. In other embodiments, air supplied to the oxygen carrying gas inlets 16 may be pressurized, thus resulting in a higher concentration of air in the plasma. In yet some other embodiments the combination of the two above methods may be used.

In addition to outputting plasma, and in some embodiments ozone and nitric oxide, the device also emits light due to the radiation from the high temperature plasma in the heating portion of the plasma channel. It has been discovered and disclosed in, for example, U.S. Pub. No. 2003004556 that a pulsed light having a dominant emissive wavelength from about 300 nm to about 1600 nm, where the duration of pulses range between 1 femtosecond to 100 seconds has various therapeutic effects. Among others, treatment of hair, epidermis, sub-surface blood vessels, and many other organs has been shown beneficial with such pulsed light. U.S. Pub. No. 2003004556 discloses various devices and methods for producing the pulsed light with required characteristics.

Figure 13:
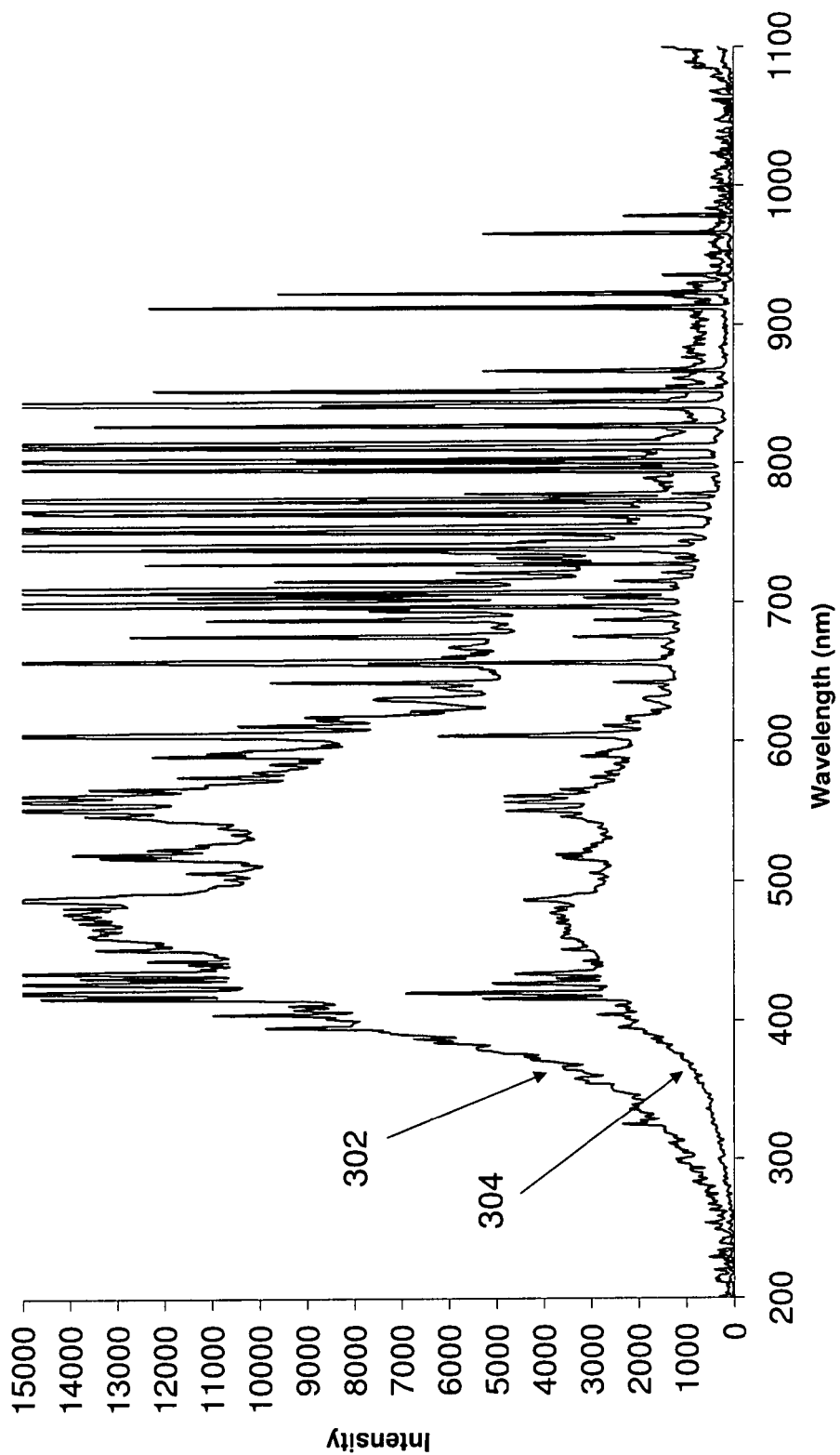
FIG. 13 illustrates a spectral distribution of light exiting the device.

As was mentioned above, the temperature of plasma in the heating portion is preferably between 8-18° kK. In this temperature range, the plasma flow emits light having a dominant emissive wavelength from about 400 nm to about 850 nm. FIG. 13 shows spectral distribution of light 302 at the distance of about 3 mm from outlet 55 and spectral distribution of light 304 at the distance of about 50 mm from the outlet 55. FIG. 13 shows the following spectral distribution:

200-350 nm—2%;
350-400 nm—5%;
400-650 nm—62%;
650-750 nm—15%;
750-850 nm—14%; and
850-1400 nm—2%.

Accordingly, device 200 may be used for pulsed light therapy in conjunction with its other uses. Note that the ratio of shorter wavelengths to longer wavelength in the spectrum of the emitted light may be easily changed by adjusting the magnitude of the current passing through the plasma flow during operational periods of pulses. With increased current, approximately the same amount of energy is used for plasma generation, but substantially more energy is used for light emission.

As for treating patients, the device may be used safely and effectively without the need to remove it from the treated tissue after each pulse, as has to be done with some prior art devices. Therefore, pulses of plasma may be generated automatically with relatively high frequency. For each pulse, a new plasma flow is generated by first passing through spark discharge and glow discharge phases, and then heating the plasma generating gas with an electric arc during the arc discharge phase. Once the plasma flow is established, it is expanded in the plasma channel by passing through the sections of the expansion portion, then the anode portion, and then the extension channel. In the extension channel, the thermal and energy density distribution of the plasma flow is modified to be substantially uniform across the cross section of the extension channel, as described above. The expanded plasma flow with the modified thermal energy distribution is safely applied to the patient's skin for the duration of the pulse. At the end of the pulse the plasma flow ceases entirely. This process can be repeated until the desired number of pulses has been delivered. The light radiation which is generated may provide benefits for treating the skin and sub-surface organs, such as dermis and blood vessels, in addition to the benefits resulting from the plasma pulses.

Extraneous matter is removed from the surface of the treated skin. Removal of extraneous matter does not have to be synchronized with pulses and may be a continuous operation. Additionally, ozone may be mixed into the plasma flow applied to the patient's skin for additional beneficial effects. As discussed above, introducing an oxygen carrying gas in the inlets of the extension portion results in formation of ozone molecules in the plasma flow.

Importantly, after a pulse of plasma is applied to the skin, the plasma flow ceases completely until the next pulse. During the off period, plasma is not applied to the patient's skin and the patient is affected only by the harmless flow of a cool plasma generating gas and the vacuum suction of the extraneous matter pump. Accordingly, an operator using the device does not risk errors associated with removal of the device from a patient's skin during the off-period and then attempting to correctly reposition the device to continue treatment. This substantially improves the safety and the duration of the procedure.

The foregoing description of the embodiments of the present invention has been presented for purposes of illustration and description. It is not intended to be exhaustive nor to limit the invention to the precise form disclosed. Many modifications and variations will be apparent to those skilled in the art. The embodiments were chosen and described in order to best explain the principles of the invention and its practical applications, thereby enabling others skilled in the art to understand the invention. Various embodiments and modifications that are suited to a particular use are contemplated. It is intended that the scope of the invention be defined by the accompanying claims and their equivalents.

What is claimed:

1. A device for generating pulses of plasma comprising:
   a. an anode;
   b. a cathode assembly comprising (i) one or more cathodes, and (ii) a cathode holder;
   c. a plasma channel, extending longitudinally between said cathode assembly and through said anode, and having an outlet opening at the anode end, a part of said plasma channel being formed by two or more intermediate electrodes electrically insulated from each other and the anode, the plasma channel comprising a heating portion closest to the cathode assembly, an anode portion, and an expansion portion between the heating portion and the anode portion, the expansion portion having two or more sections with the diameter of each successive section of the expansion portion increasing toward the anode; and d. an extension nozzle connected to the anode end of the plasma channel and forming an extension channel having a tubular insulator covering a portion of the inside surface of the extension channel.

2. The device of claim 1, further comprising a plasma chamber.

3. The device of claim 2, wherein the extension nozzle has one or more oxygen carrying gas inlets to the extension channel.

4. The device of claim 1, wherein the cathode assembly comprises two or more cathodes.

5. The device of claim 1, wherein the section of the expansion portion (i) has a diameter that is no more than 0.6 mm greater than the diameter of the adjacent section in the direction of the cathode assembly and (ii) has a length equal to or greater than its diameter.

6. The device of claim 5, wherein the section of the expansion portion closest to the cathode assembly (i) has a diameter that is no more than 0.6 mm greater than the diameter of the heating portion and (ii) has a length that is equal to or greater than its diameter.

7. The device of claim 6, wherein
   a. the diameter of the heating portion is 1.0-1.5 mm; and
   b. the length of the electrodes forming the heating portion is 1.0-2.0 times the diameter of the heating portion.

8. The device of claim 7, wherein
   a. the diameter of the anode portion is greater than the diameter of the section of the expansion portion closest to the anode by no more than 0.6 mm; and
   b. the length of the anode portion is 2.0-5.0 times its diameter.

9. The device of claim 8, wherein
   i. the inner diameter of the tubular insulator element is 1.0-1.3 times the diameter of the anode portion; and
   ii. the length of the extension channel is 2.0-3.0 times the inner diameter of the tubular insulator.

10. The device of claim 1, wherein portions of two adjacent sections of the expansion portion are formed by one intermediate electrode.

11. The device of claim 1, wherein at least one section of the expansion portion is formed by a single intermediate electrode.

12. The device of claim 1 further comprising one or more suction channels.

13. A method of treating tissue with pulses of plasma comprising repeatedly:
   a. generating a plasma flow;
   b. expanding the plasma flow to a predetermined cross-section;
   c. modifying the thermal and energy density distribution of the expanded plasma flow so the distribution is substantially uniform in the cross-section;
   d. applying the resultant plasma flow to the treated tissue; and
   e. thereafter ceasing the plasma flow.

14. The method of claim 13 wherein the energy density of each pulse is less than or equal to 5-500 $J/cm^2$.

15. The method of claim 13 further comprising removing extraneous matter from the treated tissue.

16. The method of claim 13 further comprising applying a light to the treated tissue.

17. The method of claim 16, wherein the light has a dominant emissive wavelength of 400-850 nm.

18. The method of claim 13 further comprising introducing an oxygen carrying gas into the plasma flow.

19. The method of claim 18, wherein the plasma flow applied to the treated tissue comprises particles of ozone.

20. The method of claim 19, wherein the oxygen carrying gas is air.

21. The method of claim 19, wherein the treated tissue is skin.

* * * * *